United States Patent
Watts et al.

(10) Patent No.: US 6,472,516 B1
(45) Date of Patent: Oct. 29, 2002

(54) PROGESTIN-REGULATED GENE

(75) Inventors: Colin Kenneth William Watts, Avalon (AU); Jenny Ann Hamilton, London (GB)

(73) Assignee: The Garvan Institute of Medical Research, Darlinghurst (AU)

( * ) Notice: Subject to any disclaimer, the term of this patent is extended or adjusted under 35 U.S.C. 154(b) by 0 days.

(21) Appl. No.: 09/051,961

(22) PCT Filed: Oct. 24, 1996

(86) PCT No.: PCT/AU96/00669

§ 371 (c)(1),
(2), (4) Date: Sep. 9, 1998

(87) PCT Pub. No.: WO97/15674

PCT Pub. Date: May 1, 1997

(30) Foreign Application Priority Data

Oct. 24, 1995 (AU) ............................................. PN6144
Jul. 19, 1996 (AU) ............................................. PO1128

(51) Int. Cl.⁷ ............................................. C12N 15/00
(52) U.S. Cl. .................... 536/23.5; 536/24.1; 435/69.1; 435/183; 435/194; 435/15; 435/21; 530/350
(58) Field of Search .............................. 435/69.1, 320.1, 435/15, 21, 183, 194; 536/23.5, 23.1, 24.1; 530/350

(56) References Cited

PUBLICATIONS

Bowie et al., Science 274:1306–1310, 1990.*
Skolnick et al., Trends in Biotech 18(1): 34–39, Jan. 2000.*
Zheng, Genomics 22(1):55–7, Jul. 1994.*
Ventura, Biochem.Biophys.Res.Commun. 209(3):1140–1148, Apr. 1995.*
Auffray, C.R.Acad.Sci. Iii, Sci.Vie 318(2):263–72, 1995 and Genbank AN Z24787.*
Sakai, J.Biochem. 119(3), 506–511, 1996 and Genbank D49817, Mar. 1996.*

Carson–Jurica et al., "Steriod Receptor Family: Structure and Fuctions," Endocrine Reviews, vol. 11(2):201–220 (1990).
Darville et al., "An E2F–dependent late–serum–response promoter in a gene that controls glycolyis," Oncogene, vol. 11:1509–1517 (1995).
Lange et al., "Sequence of human liver 6–phosphofructo–2–kinase/fructose–2,6–bisphosphatase," Nucleic Acids Research, vol. 18(12):3652 (1990).
Lieberman et al., "The Constitution of a Progesterone Response Element," Molecular Endocrinology, vol. 7(4):515–527 (1993).
Lively et al., "Complete Amino Acid Sequence of Rat Liver 6–Phosphofructo–2–kinase/Fructose–2,6–bisphosphatase," vol. 263(2):839–849 (1988).
Pilkis et al., "6–Phosphofructo–2–Kinase/Fructose–2, 6–Bisphosphatase: A Metabolic Signaling Enzyme," Annu. Rev. Biochem., vol. 64:799–835 (1995).
Sakata et al., "Bovine heart fructose–6–phosphate 2–kinase/fructose–2,6–bisphosphatase: Complete amino acid sequence and localization of phosphorylation sites," Proc. Natl. Acad. Sci. USA, vol. 87:4951–4955 (1990).
Sakata et al., "Molecular Cloning of the DNA and Expression and Characterization of Rat Testes Fructose–6–phosphate,2–kinase:Fructose–2,6–bisphosphatase," The Journal of Biological Chemistry, vol. 266(24):15764–15770 (1991).
Ventura et al., "Cloning and Expression of a Catalytic Core Bovine Brain 6–Phosphofructo–2–Kinase/Fructose–2, 6–Bisphosphatase," Biochemical and Biophysical Research Communications, vol. 209(3):1140–1148 (1995).
Zheng et al., "Development of 124 Sequence–Tagged Sites and Cytogenetic Localization of 217 Cosmids for Human Chrmosome 10," Genomics, vol. 22:55–67 (1994).

* cited by examiner

*Primary Examiner*—Lorraine Spector
*Assistant Examiner*—Eliane Lazar-Wesley
(74) *Attorney, Agent, or Firm*—Morrison & Foerster LLP

(57) ABSTRACT

Isolated DNA molecules are disclosed corresponding to a novel progestin-regulated gene (PRG1). The PRG1 polypeptide (PRG1) and uses thereof are also described, and include assays for assessing progestin-responsiveness in a subject.

13 Claims, 13 Drawing Sheets

```
caggctgcttcccggctcgcccaccctcctccccacgtggaagggggctggg      52
acccaaggaatgcggcccgccccgaggctgacgtacgcgtctgcggccagcc
cggactctttaaaagccggcggtgcgcggggcatccCAGCCAAGCCGGAGAG     156
GAGGCGAGCGGCAGGGCCTGGTGGCGAGAGCGCGGCTGTCACTGCGCCCGAG
CATCCCAGAGCTTTCCGAGCGGACGAGCCGGCCGTGCCGGGCATCCCCAGCC     260
TCGCTACCCTCGCAGCACACGTCGAGCCCCGCACAGGCGAGGGTCCGGAACT
TAGCCCAAAGCACGTTTCCCCTGGCAGCGCAGGAAACGCCCGGCCGCGCGCC     364
GGCGCACGCCCCCCTCTCCTCCTTTGTTCCGGGGGTCGGCGGCCGCTCTCCT
GCCAGCGTCGGGATCTCGGCCCCGGGAGGCGGGCCGTCGGGCGCAGCCGCGA     468
AGATGCCGTTGGAACTGACGCAGAGCCGAGTGCAGAAGATCTGGGTGCCCGT
              M  P  L  E  L  T  Q  S  R  V  Q
GGACCACAGGCCCTCGTTGCCCAGATCCTGTGGGCCAAAGCTGACCAACTCC     572
  K  I  W  V  P  V  D  H  R  P  S  L  P  R  S  C  G
CCCACCGTCATCGTCATGGTGGGCCTCCCCGCCCGGGGCAAGACCTACATCT
  P  K  L  T  N  S  P  T  V  I  V  M  V  G  L  P  A
CCAAGAAGCTGACTCGCTACCTCAACTGGATTGGCGTCCCCACAAAAGTGAC     676
  R  G  K  T  Y  I  S  K  K  L  T  R  Y  L  N  W  I  G
TGTCAACGTGGGGAGTATCGCCGGGAGGCTGTGAAGCAGTACAGCTCCTACA
  V  P  T  K  V  F  N  V  G  E  Y  R  R  E  A  V  K
TTCTTCCGCCCCGACAATGAGGAAGCCATGAAAGTCCGGAAGCAATGTGCCT     780
  Q  Y  S  S  Y  N  F  F  R  P  D  N  E  E  A  M  K
TAGCTGCCTTGAGAGATGTCAAAAGCTACCTGGCGAAAGAAGGGGGACAAAT
  V  R  K  Q  C  A  L  A  A  L  R  D  V  K  S  Y  L  A
TGCGGTTTTCGATGCCACCAATACTACTAGAGAGAGGAGACACATGATCCTT     884
  K  E  G  G  Q  I  A  V  F  D  A  T  N  T  T  R  E
CATTTTGCCAAAGAAAATGACTTTAAGGCGTTTTTCATCGAGTCGGTGTGCG
  R  R  H  M  I  L  H  F  A  K  E  N  D  F  K  A  F
ACGACCCTACAGTTGTGGCCTCCAATATCATGGAAGTTAAAATCTCCAGCCC
  F  I  E  S  V  C  D  D  P  T  V  V  A  S  N  I  M  E
GGATTACAAAGACTGCAACTCGGCAGAAGCCATGGACGACTTCATGAAGAGG     988
  V  K  I  S  S  P  D  Y  K  D  C  N  S  A  E  A  M
ATCAGTTGCTATGAAGCCAGCTACCAGCCCCTCGACCCCGACAAATGCGACA
  D  D  F  M  K  R  I  S  C  Y  E  A  S  Y  Q  P  L
GGGACTTGTCGCTGATCAAGGTGATTGACGTGGGCCGGAGGTTCCTGGTGAA    1092
  D  P  D  K  C  D  R  D  L  S  L  I  K  V  I  D  V  G
CCGGGTGCAGGACCACATCCAGAGCCGCATCGTGTACTACCTGATGAACATC
  R  R  F  L  V  N  R  V  Q  D  H  I  Q  S  R  I  V
CACGTGCAGCCGCGTACCATCTACCTGTGCCGGCACGGCGAGAACGAGCACA    1196
  Y  Y  L  M  N  I  H  V  Q  P  R  T  I  Y  L  C  R
ACCTCCAGGGCCGCATCGGGGCGACTCAGGCCTGTCCAGCCGGGGCAAGAA
  H  G  E  N  E  H  N  L  Q  G  R  I  G  G  D  S  G  L
GTTTGCCAGTGCTCTGAGCAAGTTCGTGGAGGAGCAGAACCTGAAGGACCTG
  S  S  R  G  K  K  F  A  S  A  L  S  K  F  V  E  E
CGTGTGGACCAGCCAGCTGAAGAGCACCATCCAGACGGCCGAGGCGCTGCGC    1300
  Q  N  L  K  D  L  R  V  W  T  S  Q  L  K  S  T  I
GGCTGCCCTACGAGCAGTGGAAGGCGCTCAATGAGATCGACGCGGGCGTCTG
  Q  T  A  E  A  L  R  L  P  Y  E  Q  W  K  A  L  N  E
TGAGGAGCTGACCTACGAGGAGATCAGGGACACCTACCCTGAGGAGTATGCG    1404
    I  D  A  G  V  C  E  E  L  T  Y  E  E  I  R  D  T
CTGCGGGAGCAGGACAAGTACTATTACCGCTACCCCACCGGGGAGTCCTACC
```

FIGURE 2B-1

```
                      Y  P  E  E  Y  A  L  R  E  Q  D  K  Y  Y  Y  R  Y
         AGGACCTGGTCCAGCGCTTGGAGCCAGTGATCATGGAGCTGGAGCGGCAGGA
            P  T  G  E  S  Y  Q  D  L  V  Q  R  L  E  P  V  I  M
         GAATGTGCTGGTCATCTGCCACCAGGCCGTCCTGCGCTGCCTGCTTGCCTAC       1508
               E  L  E  R  Q  E  N  V  L  V  I  C  H  Q  A  V  L
         TTCCTGGATAAGAGTGCAGAGGAGATGCCCTACCTGAAATGCCCTCTTCACA
               R  C  L  L  A  Y  F  L  D  K  S  A  E  E  M  P  Y
         CCGTCCTGAAACTGACGCCTGTCGCTTATGGCTGCCGTGTGGAATCCATCTA       1612
            L  K  C  P  L  H  T  V  L  K  L  T  P  V  A  Y  G  C
         CCTGAACGTGGAGTCCGTCTGCACACACCGGGAGAGGTCAGAGGATGCAAAG
               R  V  E  S  I  Y  L  N  V  E  S  V  C  T  H  R  E
         AAGGGACCTAACCCGCTCATGAGACGCAATAGTGTCACCCCGCTAGCCAGCC
               R  S  E  D  A  K  K  G  P  N  P  L  M  R  R  N  S
         CCGAACCCACCAAAAAGCCTCGCATCAACAGCTTTGAGGAGCATGTGGCCTC       1716
            V  T  P  L  A  S  P  E  P  T  K  K  P  R  I  N  S  F
         CACCTCGGCCGCCCTGCCCAGCTGCCTGCCCCGGAGGTGCCCACGCAGCTG
               E  E  H  V  A  S  T  S  A  A  L  P  S  C  L  P  P
         CCTGGACAAAACATGAAAGGCTCCCGGAGCAGCGCTGACTCCTCCAGGAAAC       1820
               E  V  P  T  Q  L  P  G  Q  N  M  K  G  S  R  S  S
         ACTGAGGCAGACGTGTCGGTTCCATTCCATTTCCATTTCTGCAGCTTAGCTT
            A  D  S  S  R  K  H  *
         GTGTCCTGCCCTCCGCCCGAGGCAAAACGTATCCTGAGGACTTCTTCCGGAG       2132
         AGGGTGGGGTGGAGCAGCGGGGGAGCCTTGGCCGAAGAGAACCATGCTTGGC
         ACCGTCTGTGTCCCCTCGGCCGCTGGACACCAGAAAGCCACGTGGGTCCCTG       2236
         GCGCCCTGCCTTTAGCCGTGGGGCCCTCACCTCCACCTCTGGGTTTCCTAGG
         AATGTCCAGCCTCGGAGACCTTCACAAAGCCTTGGGAGGGTGATGAGTGCTG       2340
         GTCCTGACAAGAGGCCGCTGGGGACACTGTGCTGTTTTGTTTCGTTTCTGTG
         ATCTCCCGGCACGTTTGGAGCTGGGAAGACCACACTGGTGGCAGAATCCTAA       2444
         AATTAAAGGAGGCAGGCTCCTAGTTGCTGAAAGTTAAGGAATGTGTAAAACC
         TCCACGTGACTGTTTGGTGCATCTTGACCTGGGAAGACGCCTCATGGGAACG       2548
         AACTTGGACAGGTGTTGGGTTGAGGCCTCTTCTGCAGGAAGTCCCTGAGCTG
         AGACGCAAGTTGGCTGGGTGGTCCACACCCTGGCTCTCCTGCAGGTCCACAC       2652
         ACCTTCCAGGCCTGTGGCTGCCTCCAAAGATGTGCAAGGGCAGGCTGGCTGC
         ACGGGGAGAGGGAAGTATTTTGCCGAAATATGAGAACTGGGGCCTCCTGCTC       2756
         CCAGGGAGCTCCAGGGCCCCTCTCTCCTCCCACCTGGACTTGGGGGGAACTG
         AGAAACACTTTCCTGGAGCTGCTGGCTTTTGCACTTTTTTGATGGCAGAAGT       2860
         GTGACCTGAGAGTCCCACCTTCTCTTCAGGAACGTAGATGTTGGGGTGTCTT
         GCCCTGGGGGGCTTGGAACCTCTGAAGGTGGGGAGCGGAACACCTGGCATCC       2964
         TTCCCCAGCACTTGCATTACCGTCCCTGCTCTTCCCAGGTGGGGACCCGGAA
         TT
```

| | | |
|---|---|---|
| PRG1 | 269 | SGLSSRGKKFASALSKFVEEQNLKDLRIVWTSQLKSTIQTAE |
| hum. liver | 274 | SGLSVRGKQYAYALANFIQSIQGISSLKVWTSRMKRTIQTAE |
| bov. brain | 283 | SGLSSRGRKFANALSKFVEEQNLKDLKVWTSQLKSTIQTAE |
| bov. heart | 273 | SGLSVRGKQFAQALRKFLEEQEIADLKVWTSQLKRTIQTAE |
| | | |
| PRG1 | 310 | ALRLPYEQWKALNEIDAGVCEEELTYEEIRDTYPEEYALREQ |
| hum. liver | 315 | ALGVPYEQWKALNEIDAGVCEEMTYEEIQEHYPEEFALRDQ |
| bov. brain | 324 | ALQLPYEQWKALNEIDAGVCEEMTYEEIKDTYPEEYALAEA |
| bov. heart | 314 | SLLGVTYEQWKILNEIDAGVCEEMTYAEIQEQYPDEFALRDE |
| | | |
| PRG1 | 351 | DKYYYRYPTGESYQDLVQRLEPVIMELERQENVLVICHQAV |
| hum. liver | 356 | DKYRYRYPKGESYEDLVQRLEPVIMELERQENVLVICHQAV |
| bov. brain | 365 | DKYYYRYPTGESYQDLVQRLEPVIMELERQENVLVICHQAV |
| bov. heart | 355 | EKYLYRYPGGESYQDLVQRLEPVIMELERQGNVLVISHQAV |
| | | |
| PRG1 | 392 | LRCLLAYFLDKSAEEMPYLKCPLHTVLKLTPVAYGCRVES- |
| hum. liver | 397 | MRCLLAYFLDKSISDELPYLKCPLHTVLKLTPVAYGCKVES- |
| bov. brain | 406 | CVCLLAYFLDKSAEEMPYLKCPLHTVLKLTPVAYGCRVES- |
| bov. heart | 396 | MRCLLAYFLDKGADELPYLRCPLHTIFKLTPVAYGCKVETL |
| | | |
| PRG1 | 433 | YLNVESVCTHRERSEDA-KKGPNPL-MRRNSVTPLASPEPT |
| hum. liver | 438 | YLNVEAVNTHREKPIENV-D-TREPEEALDTVPAHY |
| bov. brain | 447 | YLNVESVSTHRERSEDA-KKGPNPL-MRSNSH |
| bov. heart | 437 | KLNVEAVNTHRDKPTNNFPKSQTPVRMRRNSFTPLSSSNTI |
| | | |
| PRG1 | 472 | KKPRINSFEEHVASTSAALPSCLPPEVPTQLPGQNMKGSRS |
| | | |
| bov. heart | 478 | RRPRNYSVGSRPLQPLSPLRA-LDTQEGADQPKTQAETSRA |
| | | |
| PRG1 | 513 | SADSSRKH |
| | | |
| bov. heart | 518 | AHRLPSPAPPTSPS |

PROGESTIN-REGULATED GENE

This invention relates to a novel progestin-regulated gene. The protein or polypeptide encoded by this gene appears to have a novel enzymatic activity that may be useful as a readily detectable marker for progestin-responsiveness.

The sex steroid hormone progesterone has two major roles in mammalian physiology. First, progesterone is involved in preparing the uterus for implantation of the fertilized ovum. Second, progestins have proliferative and differentiating effects on mammary epithelium (1, 2). Progesterone is essential for lobuloalveolar development and preparation for lactation: when ovulation is established progesterone, produced by the corpus luteum, stimulates growth of the lobuloalveolar structures and during pregnancy promotes branching of the ductal system and differentiation of alveolar cells into secretory cells ready for milk production. The importance of progestin in these processes is clearly illustrated in progesterone receptor (PR) knockout mice, which fail to develop lobuloalveolar structures (3). Progestins may also have a role in regulating cell proliferation in the human breast. Mitotic activity in breast epithelium varies in a cyclic manner through the menstrual cycle and a role for progesterone in this process is suggested by observations that levels of this hormone and epithelial cell proliferation are both maximal during the late secretory phase (4). Some breast tumours retain progesterone responsiveness and the use of high doses of synthetic progestins are recognised endocrine therapies for PR-positive breast cancers, since in this scenario progestins have an antiproliferative effect (5). Progestins also have predominantly growth inhibitory effects on human breast cancer cell lines in vitro, although under certain conditions they may stimulate growth (2, 6 and references therein). Mechanistic studies have clearly defined both a stimulatory and inhibitory effect of progestins on breast cancer cell cycle progression (6) but the functional consequences of these effects in vivo remain to be defined. This is of considerable importance given the wide spread pharmacological usage of progestins in oral contraceptives and in hormone replacement therapy.

The mechanisms underlying the biological effects of progestins in the normal breast and in breast cancer are only partially understood. Progestin action is mediated primarily via the PR, which upon activation by ligand binding interacts with gene promoter sequences containing progesterone responsive elements (PREs) to regulate gene transcription. Very few mammalian genes have been described that are directly regulated by progestins in this manner: examples include c-jun (7), cfos (8), fatty acid synthetase (FAS) (9), PR (10, 11), and uteroglobin (12, 13). While progestin action ultimately involves changes in the levels of large numbers of mRNAs and proteins, many of these require intermediary de novo protein synthesis. Furthermore, specific genes that mediate the proliferative effects of progestins are likewise poorly defined. Thus much remains to be learned about genes induced as an acute response to progestin treatment and their role in mediating progestin effects on cell proliferation and differentiation.

Several known progestin-regulated genes can be classed as those whose functions are important in differentiation effects mediated by progestin. Examples include FAS (9), alkaline phosphatase (14) and lactate dehydrogenase (15). While these are probably not involved in the proliferative effects of progestin a number of progestin-related genes related to steroid and growth factor action might contribute to these effects at least indirectly. Examples include estrogen receptor (16), PR (11), retinoic acid receptors (17), epidermal growth factor receptor (6, 18), prolactin receptor (19), insulin-like growth factors α and β1 (6, 8, 23, 24), 17β-hydroxysteroid dehydrogenase (25) and insulin-like growth factor binding proteins 4 and 5 (26). However, evidence that these gene products are direct mediators of the stimulatory and inhibitory effects of progestins remains to be determined. Potentially of more interest are progestin-regulated genes with known roles in cell cycle control i.e. c-myc, c-fos (6, 8), c-jun (7) and cyclin D1 (27). Progestin induction of c-myc and cyclin D1 is closely related to changes in cell cycle progression (6, 27). While the timing of the induction of c-myc mnRNA, evident after 30 min. of progestin treatment, suggests a potential direct effect of progestins, the slower induction of cyclin D1 MRNA which is maximal at 6 hours could result from the prior induction of other genes that are the primary and specific targets of progestins. Given the established central role for cyclin D1 in steroid and growth factor regulation of breast cancer cell cycle progression (27–30) identification of progestin regulated genes which control cyclin D1 gene expression might link progestin action to the cell cycle.

Using serum-free conditions, studies in this laboratory have shown that T-47D human breast cancer cells which were stimulated to grow with insulin, undergo a transient increase in cell cycle progression in response to progestins. with an increased rate of progression through G1 and a transient increase in the S-phase population. These cells complete a round of replication and thereafter become growth arrested early in G1 phase.

The present invention arose out of a study using this model system to identify novel progestin regulated genes involved in early cell cycle stimulatory responses to progestin or other aspects of progestin action in human breast cancer cells. RNA extracted from T-47D cells grown under serum-free conditions and treated with the synthetic progestin ORG 2058 for 3 hours was used as the template for cDNA synthesis and analysis by the differential display technique (mRNA fingerprinting) (31). Several candidate PCR fragments were identified by this method and characterisation by sequence and Northern analysis of some of these led to the identification and characterisation of a clone. PRG1, which appears to represent a novel progestin-regulated gene.

Thus, in a first aspect, the present invention provides an isolated DNA molecule comprising a nucleotide sequence substantially corresponding or, at least, >80% (more preferably, >90%) homologous to any one of the nucleotide sequences shown at:

(i) FIG. 2B from nucleotide 1 to 3018;
(ii) FIG. 2B from nucleotide 1 to 470;
(iii) FIG. 2B from nucleotide 141 to 3018: and
(iv) FIG. 2B from nucleotide 470 to 2103.

Preferably. the isolated DNA molecule is of human origin. More preferably, the isolated DNA molecule is of human kidney cell or breast cancer cell origin, and/or encodes a protein normally expressed in human kidney cells, breast tissue or tumour cells.

The isolated DNA molecule may be incorporated into plasmids or expression vectors. which may then be introduced into suitable bacterial, yeast and mammalian host cells. Such host cells may be used to express the polypeptide encoded by the isolated DNA molecule.

The predicted amino acid sequence of the polypeptide encoded by PRG1 shows substantial homology (~70%) with human liver 6-phosphofructo-2-kinase/fructose 2.6 bisphosphatase (PFK-2/FBPase-2) and it is postulated that the protein encoded by PRG1 may have activities similar to this bifunctional enzyme.

Thus, in a second aspect, the present invention provides a polypeptide in a substantially pure form, said polypeptide comprising an amino acid sequence substantially corresponding to that shown at FIG. 2B or an enzymatic portion thereof.

Preferably, the polypeptide of the second aspect is full length.

The polypeptide of the second aspect may be used to raise monoclonal or polyclonal antibodies which may be used, for example, in affinity purification processes or in various ELISA type assays.

Thus, in a third aspect, the present invention provides an antibody specific to the polypeptide of the second aspect.

As will be seen hereinafter, PRG1 appears to be directly regulated by progestin. PRG1 may, therefore, provide a useful marker for progestin-responsiveness in a subject. For example, as a marker of breast tumour responsiveness to progestins—i.e. high levels may indicate that the tumour is responsive to progestins and could be sensitive to progestin therapy. PRG1 may also be a useful prognostic marker since hormonally responsive tumours often have a better prognosis (i.e. patients have longer disease-free survival and overall survival). Thus, levels of PRG1 MRNA present in isolated cells or tissue samples may be assessed by DNA or RNA probes or primers in hybridisation assays or PCR analysis. Suitable probes and primers, which are preferably of a length greater than 10 nucleotides, are to be considered as forming part of the present invention. Alternatively, the level of PRG1 polypeptide may be assessed through the use of the abovementioned antibodies. However, the postulated enzymatic activity of the PRG1 polypeptide provides the potential for a more convenient assay wherein the level of PRG1 polypeptide would be determined by assessment of enzyme activity.

Thus, in a fourth aspect, the present invention provides as assay for assessing progestin-responsiveness in a subject comprising the steps of;
(i) isolating cells or tissue from said subject; and
(ii) detecting the presence of a polypeptide comprising an amino acid sequence substantially corresponding to that shown at FIG. 2B.

Preferably, the polypeptide detection step involves providing a substrate for said polypeptide, said substrate normally converted by said polypeptide to a readily detected product.

In some circumstances, it may be preferred to expose the isolated cells or tissue to progestin or an agonist compound and, subsequently, determine whether the progestin or agonist compound has induced the production of PRG1 polypeptide.

The postulated enzyme activity of the PRG1 polypeptide also suggests that this polypeptide has an involvement in cell cycle (growth) regulation and is likely to be involved in control of glycolytic/gluconeogenic/lipogenic pathways not only in progestin target tissues but in a wide range of different tissue types. Indeed, since PRG1 appears to be expressed in tissues with a probable low fraction of proliferating cells it is unlikely that the function of the PRG1 polypeptide is restricted to growth regulation. More likely, PRG1 is more generally involved in glycolytic/gluconeogenic/lipogenic control. This may be of particular significance as the other related human enzyme PFK-2/FBPase-2, which has an established important role in glycolytic control, has only a limited tissue distribution (e.g. liver). Thus, the administration of PRG1 polypeptide may be of significant therapeutic value particularly for treatment of diabetes, obesity or other disorders of energy metabolism. Therapeutic amounts are likely to be similar to normal endogenous levels (which will vary from tissue to tissue) or may be at significantly higher levels, depending on the level and type of activity desired.

Alternatively, the enzyme activity of the PRG1 polypeptide could be regulated by pharmacological means for the treatment of proliferative disorders, such as malignant or non-malignant hyperproliferative disease (e.g. breast and other cancers, and dermatological diseases). Further, administration of PRG1 polypeptide may be of therapeutic value in the control of reproductive function.

More specifically, the enzyme activity of the PRG1 polypeptide could be regulated by;
synthetic compounds, either stimulatory or inhibitory (i.e. agonists or antagonists),
ribozymes specific for PRG1 (i.e. to down-regulate endogenous PRG1 activity), and
gene therapy using expression vectors or oligonucleotides or other delivery systems (e.g. viral) containing a nucleotide sequence encoding PRG1 sense (i.e. to augment endogenous PRG1 polypeptide levels and activity) or antisense (i.e. to down-regulate endogenous PRG1 levels and activity).

Agonist or antagonist compounds could be identified by their ability to inhibit/stimulate the enzyme activity of PRG1 polypeptide. For example, screening assays could be conducted to identify compounds that modulate 6-phosphofructo-2-kinase activity by measuring the rate of production of fructose-2,6-biphosphate from fructose-6-phosphate (assaying fructose-2,6-biphosphate by its ability to activate pyrophosphate-dependent 6-phosphofructo-1-kinase from potato tubers) (58). Alternatively, screening assays could be conducted to identify compounds that modulate fructose-2,6-biphosphatase activity by measuring [$^{32}$P] release from [2-$^{32}$P] fructose-2,6-bisphosphate (59). Such screening assays may be performed using in vitro systems such as dissolved pure PRG1 polypeptide or a whole cell lysate of cells expressing PRG1.

Such agonist and antagonist compounds may include compounds which influence enzymatic activity by a number of mechanisms such as the alteration of substrates to the enzyme's active site(s), either by acting as alternative substrates or by binding to PRG1 polypeptide to alter its structure, or by influencing processes involved in the activation of the PRG1 polypeptide (e.g. phosphorylation of regulatory domains).

Results provided hereinafter strongly suggest that induction of PRG1 by progestin is a direct transcriptional effect of ligand-activated PR on a putative progestin-regulatory element(s) (PRE) located within the PRG1 gene, Thus, in a fifth aspect, the present invention provides an isolated DNA molecule comprising a progestin-regulatory element (PRE) derived from a DNA molecule according to the first aspect of the invention.

The DNA molecule of the fifth aspect may be used as a controlling element for PRG1 (and potentially for other genes containing similar promoter elements), for novel therapeutics to control gene expression or could be utilised in DNA constructs designed to express RNA/protein sequences in response to progestins (e.g. progestin-inducible plasmids) which could be useful as research tools for studying gene expression in cell lines. The DNA molecule of the fifth aspect could also be of use in gene therapy directed to progestin-responsive tissues e.g. breast, uterus.

The term "substantially corresponds" as used herein in relation to the nucleotide sequence is intended to encompass minor variations in the nucleotide sequence which due to degeneracy in the DNA code do not result in a change in the encoded protein. Further, this term is intended to encompass other minor variations in the sequence which may be required to enhance expression in a particular system but in which the variations do not result in a decrease in biological activity of the encoded protein.

The term "substantially corresponding" as used herein in relation to amino acid sequence is intended to encompass minor variations in the amino acid sequence which do not result in a decrease in biological activity of the encoded protein. These variations may include conservative amino acid substitutions. The substitutions envisaged are: G,A,V,I, L.M: D, E; N,Q; S,T; K,R,H; F,Y,W,H; and P,Nα-alkalamino acids.

The invention will now be further described with reference to the following non-limiting example and accompanying figures.

BRIEF DESCRIPTION OF THE FIGURE

FIG. 3: Amino acid sequence homologies of human and bovne PFK-2FBPase-2 isoforms.
Amino acid sequence homology between PRG1 (SEQ ID NOS:1) and PFK-2/FBPase-2 isoforms from human liver, bovine brain and bovine heart (SEQ ID NOS:7–9). An alignment of the amino acid sequences was obtained using the computer programs MacVector™ 4.5.3 and SeqVu. Identical residues found in three or four of the polypeptides are boxed. Amino acids are numbered from the first residue. The bovine brain sequence is believed to be incomplete (39). Bov., bovine; hum., human.

B) T-47D cells proliferating in medium supplemented with 5% charcoal-treated FCS were treated with livial (10 nM) and ethanol vehicle in the presence and absence of actinomycin D (5 μg/ml) and harvested for Northern analysis. The Northern blot was probed with a 1.8 kb cDNA sub-clone of PRG1. C, ethanol control; L, livial.

Figure 9:
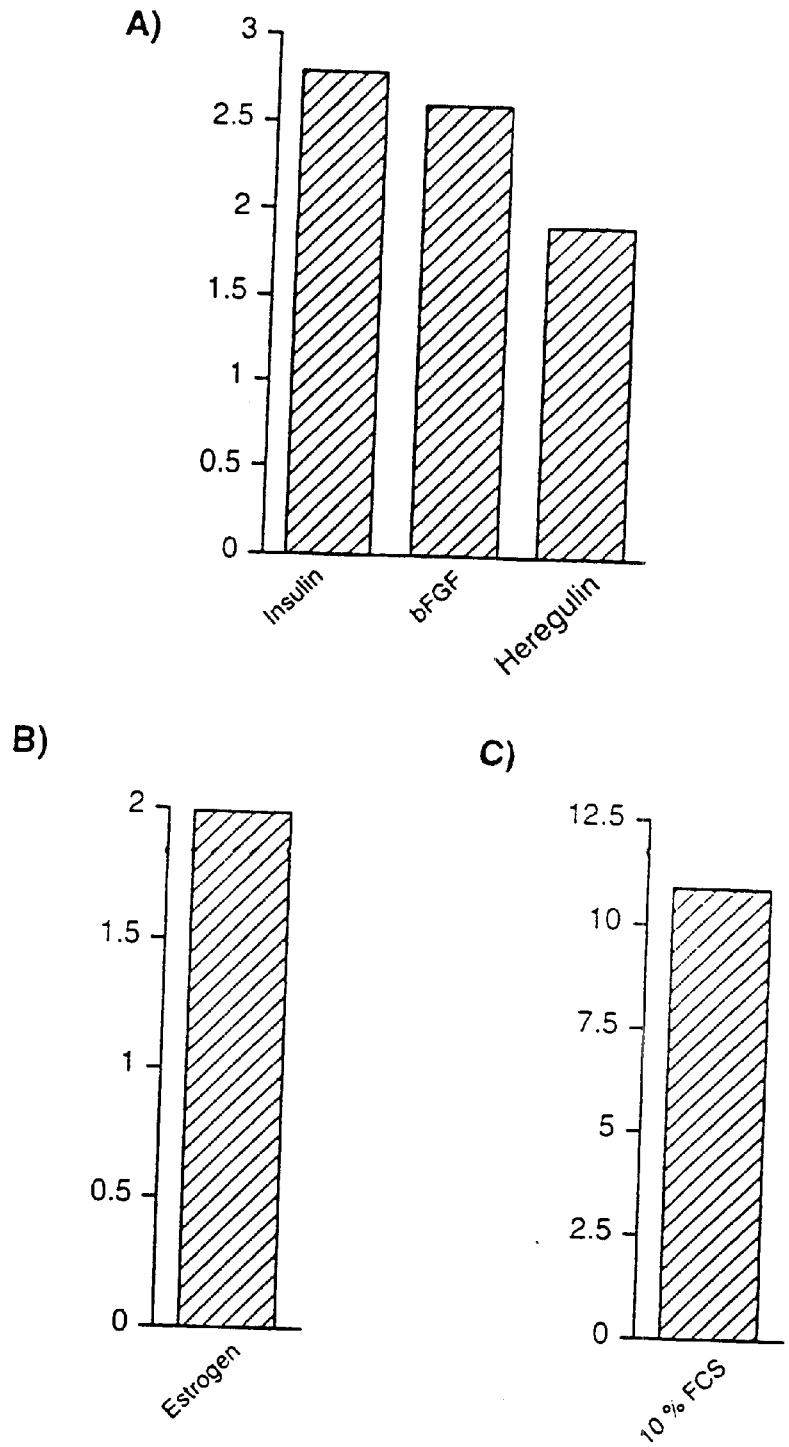

FIG. 9: PRG1 mRNA regulation by breast cancer cell mitogens.

Northern blots were probed with a 1;8 kb cDNA sub-clone of PRG1 and with an oligonucleotide complementary to 18S rRNA as a loading control. Densitometric analysis, adjusted for loading, of the autoradiographs is presented.

A) Total RNA was isolated from T-47D cells growth arrested by serum deprivation and then stimulated to progress through the cell cycle by addition of insulin (1.7 μM), bFGF (55 pM) or heregulin (5 nM). PRG1 mRNA levels were measured at 3 or 4 h. and expressed relative to time matched vehicle treated controls.

B) Total RNA was isolated from MCF-7 cells rescued with estrogen (17βv estradiol, 100 nM) following pre-treatment with antiestrogen (ICI 182780, 10 nM) for 48 h. in 5% fetal calf serum. PRG1 mRNA levels were measured at 4 h. and expressed relative to the average of antiestrogen treated control samples.

C) Total RNA was isolated from T-47D cells growth arrested by serum deprivation or exponentially growing in medium containing 10% fetal calf serum. PRG1 mRNA levels from exponentially growing cells are expressed relative to PRG1 mRNA levels from growth arrested cells.

Figure 10:
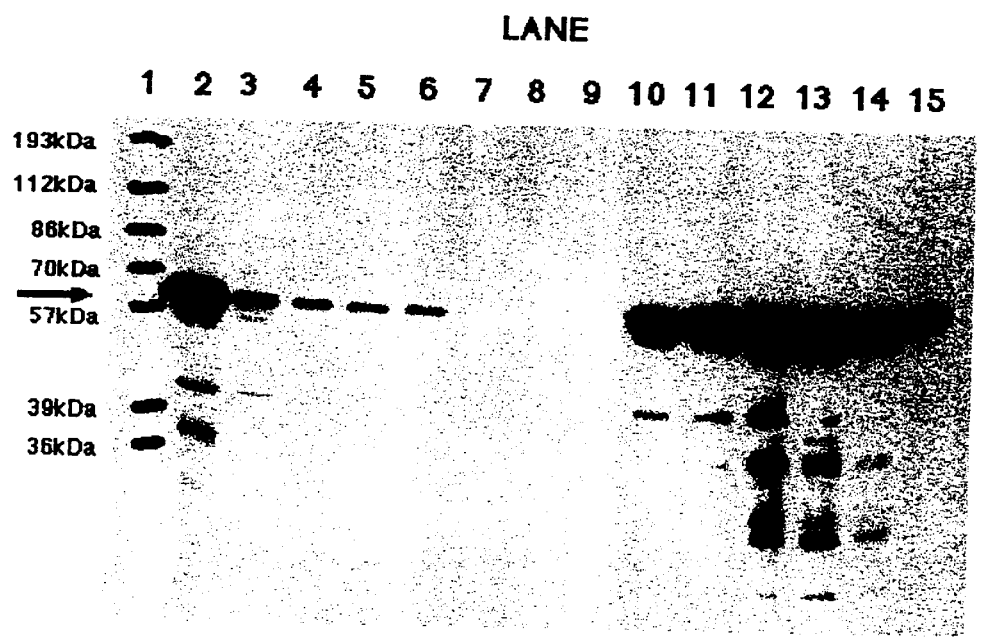

FIG. 10: Affinity purification of FLAG PRG1 fusion protein.

PRG1 fusion protein was expressed in bacteria, purified samples run on a 10% SDS-PAGE gel and Western blotted with an anti-FLAG antibody as described in the Materials and Methods. Lane 1, molecular weight markers; lane 2, soluble bacterial lysate as loaded on column; lanes 3–6, flow through; lanes 7–9, washes 1, 4, 5; lanes 10–15, fractions 1–6. The position of the FLAG PRG1 fusion protein is marked with an arrow.

EXAMPLE

Materials and Methods

Reagents

Steroids and growth factors were obtained from the following sources: ORG 2058 (16α-ethyl-21-hydroxy-19-norpregn-4-en-3,20-dione), Amersham Australia; R5020 (17α-21-dimethyl-19-norpregn-4,9-diene-3,20-dione), Du Pont (Australia) Ltd; MPA (17α-acetoxy-6α-methyl-4-pregn-4-en-3,20-dione), Dr. Dudley Jacobs of Upjohn Pty Ltd, Australia; livial ((7α, 17α)-17-hydroxy-7-methyl-19-norpregn-5(10)-en-20-yn-3-one), Dr. William Schoonen of Organon International, Oss, The Netherlands; RU 486 (17β-hydroxy-11β-(4-methylaminophenyl)-17β-(1-propynyl)-etsra-4,9-diene-3-one), Dr John-Pierre Raynaud of Roussel-Uclaf, Romainville, France; ICI 182780 (77β-[9-(4,4,5,5,5-pentafluropentylsulfinyl)nonyl] estra-1,3,5(10)-triene-3, 170β-diol) was a gift from Dr. Alan Wakeling, (Zeneca Pharmaceuticals, Macclesfield, UK); dexamethasone (9-fluro-11,17,21-trihydroxy-16-methylpregn-1,4-diene-3, 20-dione) and 17β-estradiol, Sigma Chemical Co., St. Louis, Mo.; human insulin, Actrapid; CSL-Novo, Australia; human recombinant bFGF was donated by Dr. A. Protter, Pacific Biotechnology, Sydney, Australia and recombinant heregulin was produced by Drs. Rod Fiddes, CRC for Biopharmaceutical Research and Dr. Roger Daly, Garvan Institute of Medical Research (32). Steroids were stored at −20° C. as 1000-fold-concentrated stock solutions in absolute ethanol. Growth factors were stored at −20° C. and diluted on the day of use; bFGF in 30 μM human transferrin (Sigma Chemical Co., St. Louis, Mo.); heregulin as described (32). Insulin was stored at 4° C. and used diluted directly in tissue culture medium. Cycloheximide (Calbiochem-Behring Corp., La Jolla, Calif.) was dissolved at 20 mg/ml in water and filter sterilized. Cosmegen, actinomycin D, (Merck Sharp and Dohme Research Pharmaceuticals, Rahway, N.J.) was dissolved at 0.5 mg/ml in sterile water and used immediately. Tissue culture reagents were purchased from standard sources.

Cell Culture

The sources and maintenance of the human breast cancer cell lines used in this study were as described previously (33). 184 and 184B5 normal breast epithelial cells were the kind gift of Dr. M. Stampfer (University of California, Berkley, Calif.) and were maintained in mammary epithelial growth medium (Clonetics, San Diego, Calif.). Tissue culture experiments in serum-free medium were performed as previously described (6, 27). Briefly, T-47D cells were taken from stock cultures and passaged for 6 days in phenol red-free RPMI medium supplemented with 10% charcoal-treated fetal calf serum (FCS). During this time the cells received two changes of medium at 1- to 3-day intervals. The cells were replated into replicate 150 cm$^2$ flasks in medium containing 10% charcoal-treated FCS and the medium replaced with serum-free medium on the next two days. Serum-free medium was supplemented with 300 nM human transferrin. In experiments involving ORG 2058 the final serum-free medium contained 10 μg/ml (1.7 μM) human insulin. Three days after completion of these pre-treatments growth factor, steroid, steroid antagonist or cycloheximide were added. Control flasks received vehicle to the same final concentration. Cell cycle phase distribution was determined by analytical DNA flow cytometry, as previously described (6, 34).

Tissue culture experiments in serum-containing medium were performed as previously described (34). The experiment with livial and actinomycin D was as for experiments in serum-containing medium except that the medium contained 5% charcoal-treated FCS. Actinomycin D was added at the same time as livial. The experiment involving "estrogen rescue" was performed as described (30). Briefly, MCF-7 cells were cultured in medium containing 5% FCS for 2 days. The antiestrogen ICI 182780 (10 nM) was then added to the medium for 48 h. after which the growth-arrested cells were treated with 100 nM 17β-estradiol, also added directly to the medium, resulting in the synchronous re-entry of cells into the cell cycle.

RNA Isolation and Northern Analysis

Cells harvested from triplicate 150 cm$^2$ flasks were pooled and RNA extracted by a guanidinium-isothiocyanate-cesium chloride procedure and Northern analysis was performed as previously described with 20 μg of total RNA per lane (6, 11). The membranes were hybridized overnight at 50° C. with probes labelled with [α-$^{32}$P] dCTP (Amersham Australia Pty Ltd, Castle Hill, Australia) using the Random Prime Labelling Kit (Promega, Sydney, Australia). The membranes were washed at a highest stringency of 0.2× SSC (30 mM NaCl. 3 mM sodium citrate [pH 7.0])+ 1% sodiwn dodecyl sulfate at 65° C. and exposed to Kodak X-OMAT or BIOMAX film at −70° C. Human multiple tissue Northern blots (Clontech Laboratories, Inc. Palo Alto, Calif.) were hybridized under conditions recommended by the manufacturer. The mRNA abundance was quantified by densitometric analysis of autoradiographs using Molecular Dynamics Densitometer and software (Molecular Dynamics, Sunnyvale, Calif.). The accuracy of loading was estimated by hybridizing membranes with a [$\gamma$-$^{32}$P]ATP end-labelled oligonucleotide complementary to 18S rRNA.

Differential Display

Differential display was carried out as described (35). Total RNA, 200 ng, obtained from T-47D cells treated with the synthetic progestin ORG 2058 for 3 h. or from T-47D cells treated with ethanol control was reverse transcribed with 5'-T$_{12}$GG as the primer. The cDNA products were amplified by the polymerase chain reaction (PCR) using 5'-T$_{12}$GG and 5'-CAAACGTCGG primers. The PCR products were separated on a 6% polyacrylamide denaturing sequencing gel. The PCR product of interest was excised from the gel, re-amplified by PCR and cloned into the pGEM-T vector (Promega). DNA sequencing was performed by the dideoxy chain termination method using T7 DNA polymerase (AMRAD Pharmacia Biotech, Melbourne, Australia) and Sequenase 2.0 kit (Bresatec, Adelaide, Australia) or by cycle sequencing using the fmol ® DNA Cycle Sequencing System (Promega). Sequence database searches were performed at the NCBI using the BLAST network service.

Library Screening

The differential display technique generates small (<500 nt) cDNA fragments. In order to obtain additional cDNA sequence lambda cDNA libraries derived from human kidney (Clontech, 2.85×10$^5$ pfu) and human heart (Stratagene, La Jolla, Calif. 6×10$^5$ pfu) were screened using the $^{32}$P-labelled differential display cDNA fragment as a probe under stringent hybridization conditions. Seven strongly hybridizing clones were isolated and excised for sequencing using bacterial strain XL1-Blue. Sequencing was performed as described above. Amino acid sequence alignments were performed using the computer programs MacVector™ 4.5.3 and SeqVu.

Expression of PRG1 Protein in Bacteria

Clones 11.2 and 19.1 (FIG. 2) were cloned as Eco R1 fragments into pBluescript (pBS11.2 and pBS19.1). An Xba 1/Nco 1 fragment from pBS19.1 was then ligated to replace an Xba 1/Nco 1 fragment from pBS11.2. The resultant plasmid contained the complete PRG1 open reading frame. PCR using this plasmid and the forward primer 5'ATGAATTCATGCCGTTGGAACTGACGCAGAGC-3' (SEQ ID NO:4) and the reverse primer 5'-TACCTAGTCGACTCAGTGTTTCCTGGAGGAGTCAGC-3' (SEQ ID NO:5) was then performed to generate a full length open reading frame sequence with the appropriate terminal sequences that could next be cut with Eco R1 and Sal 1. The resulting fragment was cloned into the bacterial expression vector pFLAG=AE-2 (Eastman Kodak Company, New Haven, Conn., USA). E. Coli (DH5a strain) were then transformed with this construct and used to innoculate L-broth (containing 0.4% glucose) at a 1:100 dilution. The culture was grown to OD600 approx 0.4. Expression of the FLAG PRG1 fusion protein was induced by the addition of IPTG (0.5 mM final concentration). continuing incubation for 1 hr at 30° C., shaking at 240 rpm.

To prepare the soluble fraction, bacteria from a 500 ml culture were resuspended in 50 ml of extraction buffer A (50 mM Tris HCl, pH 8.0, 5 mM EDTA, 0.25 mg/ml lysozyme, 50 $\mu$g/ml sodium azide). Extraction Buffer B (5 ml) was then added (1.5 M NaCl. 0.1 M CaCl2, 0.1 M MgCl2. 0.02 mg/ml DNAse I. 0.05 mg/ml aprotonin). The bacterial lysate was then centrifuged at 25000 g for 1 hour. The supernatant represents the soluble lysate fraction. To purify the PRG1 fusion protein. 50 ml of the soluble fraction was loaded onto a column containing 1 ml of anti-FLAG M2 affinity gel (Eastman Kodak Company, New Haven, Conn. USA). The column flow rate was 0.5 ml/min. The column was then washed with 4×9 ml of TBS (50 mM Tris-HCl, 150 mM NaCl at a final pH of 7.4 ). The bound fusion protein was then eluted with 0.1 M glycine pH 3.0 (1 ml+10×0.5 ml). Aliquots from each fraction were run on 10% SDS -PAGE gel together with pre-stained molecular weight markers (Sigma) and Western blotted with ananti-FLAG M2 antibody (Eastman Kodak Company, New Haven, Conn. USA).

Results

Cloning of a cDNA Identified by Differential Display

Figure 1:
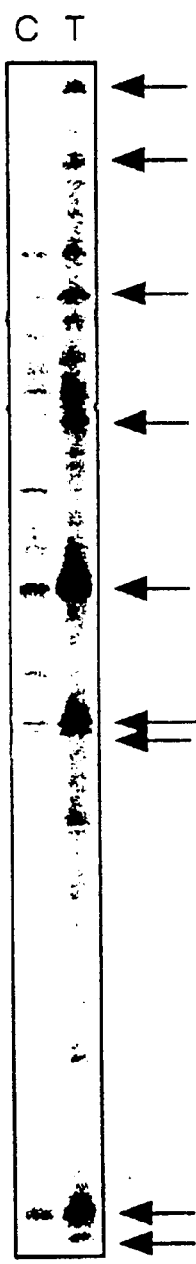
FIG. 1: Identification of differentially expressed cDNAs in T-47D cells treated with the synthetic progestin ORG 2058.
A) Identification of PIG1 by differential display. Total RNA obtained from T-47D cells treated with ORG 2058 or ethanol for 3 h. was used as a template for differential display PCR reactions with 5'-$T_{12}$GG and 5'-CAAACGTCGQ (SEQ ID NO:3 ) as primers. The PCR products were separated on a 6% polyacrylamide denaturing gel and the gel exposed to x-ray film. The arrows indicate PCR products present at a higher level in progestin treated (T) compared with ethanol control (C).
B) Confirmation of the progestin induction of PIG1 by Northern analysis. T-47D cells proliferating in insulin-supplemented serum-free medium were treated with 10nM ORG 2058 (T) or ethanol vehicle (C) for 3 h and total RNA was harvested for Northern analysis. The Northern blot was probed with the PIG1 fragment.
Figure 1:
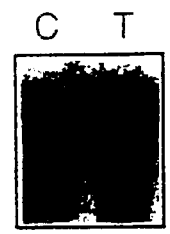

The differential display technique was used to identify mRNAs expressed in T-47D human breast cancer cells whose levels of expression had altered in response to treatment with the synthetic progestin ORG 2058 for 3 h. Using the PCR primer combination 5'-T$_{12}$GG and 5'-CAAACGTCGG (SEQ NO.:3)a total of 9 cDNA fragments identified by gel electrophoresis were clearly upregulated (FIG. 1A). Preliminary confirmatory screening by Northern analysis showed one of the cDNA fragments, designated PIG1 (described in the Applicant's Australian Provisional Patent Application No. PN6144), was induced rapidly in the presence of ORG 2058 (FIG. 1B) and therefore warranted further characterisation.

Figure 2A:
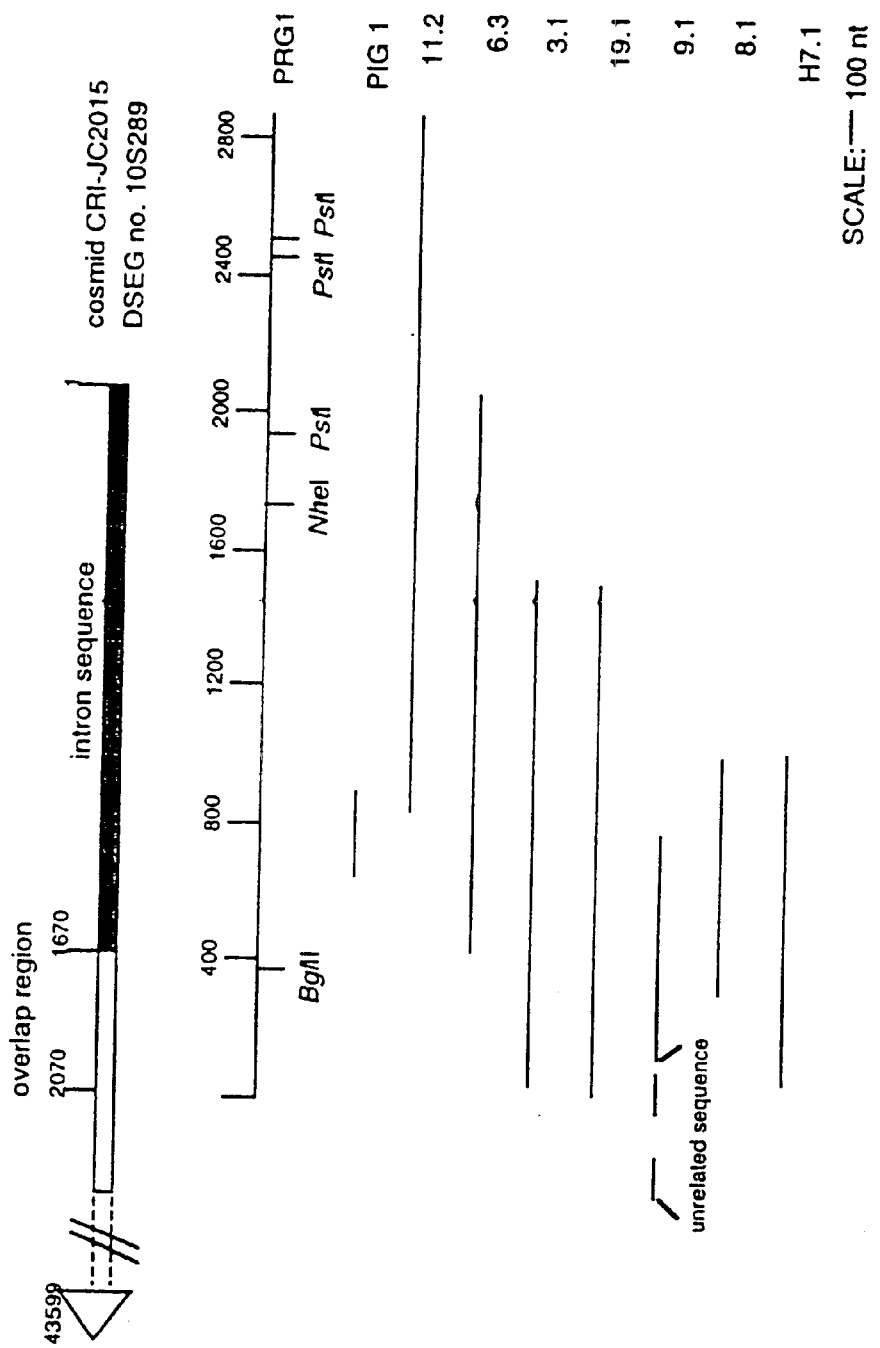
FIG. 2: Determination of the PRG1 cDNA sequence.
A) A schematic representation of PRG1 structure with a restriction map for the PRG1 cDNA and the cDNA clones used to derive the PRG1 sequence shown beneath. The initial PCR cDNA fragment identified by differential display was designated PIG1. All the cDNA clones were isolated from a human kidney cDNA library with the exception of H7.1 which was isolated from a human heart cDNA library. Clone 19.1 is a chimeric clone. The cosmid clone containing genomic sequence, part of which overlaps with PRG1 cDNA sequence, was obtained from the Genbank database and is shown above the PRG1 sequence. The numbers refer to distances in nucleotides.
B) Nucleotide and deduced amino acid sequence (SEQ ID NOS:1–2) of PRG1. The nucleotide sequence determined from cDNA clones is shown in uppercase lettering whereas the nucleotide sequence obtained from the cosmid genomic clone CR1-JC2015 is shown in lower-case lettering. The translation termination codon is shown by an asterisk in the amino acid sequence. The in-frame termination codon that precedes the initiating methionine is underlined. The numbers refer to distances in nucleotides.

In order to obtain the complete coding sequence from which PIG1 was derived, a human kidney cDNA library constructed using oligo-dT-primed and random-primed cDNA was screened using the PIG1 fragment. Four cDNAs were isolated after screening 2.85×105 recombinants, namely 11.2, 6.3, 3.1 and 19.1 (FIG. 2A). Further screening of this library with an oligonucleotide derived from 5' sequence of 3.1 (5'-ACCGTCATCGTCATCGGTGGG-3' (SEQ. ID. NO:6)) and with a 373; nt EcoR1-Bg/II restriction fragment derived from 3.1.1 resulted in the isolation of a chimeric clone 9.1 and clone 8.1 (FIG. 2A). Screening of a human heart library with the 373 nt EcoR1-Bg/II restriction fragment resulted in the isolation of clone H7.1 (FIG. 2A). Clones 11.2, 6.3, 3.1 were sequenced in their entirety on both strands, and 350 nucleotides of the 5' end of clone 19.1 were sequenced on both strands, to give 2887 nt of cDNA sequence, designated PRG1, shown in uppercase lettering (FIG. 2B). While the 2887 nt of sequence is less that the mRNA size determined from Northern blots it contains a complete open reading frame as discussed below.

Comparison of the cDNA sequence with the GenBank and EMBL databases revealed a partial overlap with a cosmid clone (CRI-JC2015) (36) containing human genomic sequence from chromosome 10. Nucleotides numbering 1–399 of the cDNA overlap with nucleotides 1671–2070 from the cosmid clone but in the reverse orientation (FIG. 2A). Nucleotides 1670–1 of the cosmid clone are not present in PRG1 and appear to be intron sequence as the consensus splicing nucleotides, GT, which commonly flank the start of introns (37) are present at bases 1670 and 1669, respectively. Extrapolating backwards 27 nucleotides from the 5' end of the cDNA into the genomic sequence reveals an in-frame stop codon, refer to FIG. 2B where the genomic sequence is shown in lowercase lettering.

Analysis of the PRG1 cDNA sequence identified an open reading frame (ORF) containing 520 amino acids encoding a polypeptide very similar to human liver 6-phosphofructo-2-kinase/fructose--2.6-bisphosphatase (PFK-2/FBPase-2) (38) as well as to bovine brain and heart forms of this enzyme (39, 40). PRG1 bears 72% amino acid identity with the human liver PFK-2/FBPase-2 in 447 amino acid overlap and 93% and 74% identity with bovine brain PFK-2/FBPase-2 and bovine heart PFK-2/FBPase-2 in 462 amino acid and 447 amino acid overlap, respectively (FIG. 3). The ORF identified in the PRG1 cDNA sequence appears to be complete. The initiation codon preceded by an in-frame stop codon located 357 nucleotides upstream as identified in the cosmid clone (CRI-JC2015) and the initiating methionine is within close proximity of initiating methionines of other known related polypeptides (examples 38. 40–42) with the exception of the bovine brain PFK-2/FBPase-2, the sequence of which is incomplete (39).

Analysis of the deduced amino acid sequence of PRG1 using the Prosite Database Release 13.0 revealed several consensus phosphorylation sites, three for cyclic AMP and cyclic GMP dependent protein kinases beginning at residues 53, 189, 458, seven for protein kinase C beginning at residues 52, 129, 272, 441, 471, 516, 517, eleven for casein kinase II at residues 129, 153, 171, 192, 333, 340, 362, 403, 441, 478, 512 as well as two for tyrosine kinases beginning at residues 348, 402. Consensus sequences for one N-glycosylation site. three N-myristoylation sites and two amidation sites were detected beginning at residues 128, 118, 266, 509, 218, 274, respectively. In addition the ATP/GTP-binding site signature motif, conserved in all mammalian forms of PFK-2/FBPase-2 (43), was identified as amino acids 42–49 as was the phosphoglycerate mutase family phosphohistidine signature. amino acids 51–60.

Northern Blot Analysis of PRG1 Gene Expression

The expression profile of PRG1 in a panel of human breast cancer and normal breast cell lines was investigated by hybridizing Northern blots of total RNA isolated from 1 normal breast epithelial cell strain (HMEC 184), 2 transformed normal epithelial cell lines (HMEC 184B5 and HBL-100) and 12 breast cancer cell lines (only 9 are shown) to a probe from a 1.8 kilobase (kb) cDNA sub-clone, 6.3.1 (FIG. 2A), which contains 98% of the PRG1 ORF. PRG1 mRNA, a single transcript of -4.4 kb, was expressed in all the breast cancer and normal breast epithelial cell lines examined (FIG. 4A). The highest level of expression was in the T-47D cell line and the lowest levels were noted in SK-BR-3 (not shown), BT-474, HBL-100, HMEC 184 and HMEC 184B5 cell lines. There was no correlation between PRG1 mRNA expression and estrogen receptor (ER), progesterone receptor (PR) or glucocorticoid receptor (GR) status (44) although the T-47D cell line, which expresses PR at a level 5-fold higher than the other cell lines had the highest level of expression (45).

The tissue specificity of PRG1 gene expression was also investigated by hybridizing Northern blots of poly A+ RNA isolated from a variety of human tissues to a probe made from the sub-clone 6.3.1. A 4.4 kb transcript was detected in all the tissues examined (FIG. 4B). The apparent abundance of PRG1 mRNA in skeletal muscle shown in FIG. 4B may be the result of uneven mRNA loading as in a second set of human tissue poly A+ Northern blots skeletal muscle mRNA levels were similar to those of the kidney. Likewise, colon showed a higher level of expression in the second set of Northern blots. In the heart and skeletal muscle a band of 1.35 kb was also detected. This band was more easily detected under lower stringency conditions when it was also found to be present in kidney, pancreas, skeletal muscle and colon (data not shown) and suggests that the cDNA PRG1 probe was cross-reacting with a related sequence. A third transcript of around 9.5 kb was also detected in skeletal muscle.

PRG1 mRNA is Induced Transiently by Proyestin

Figure 5:
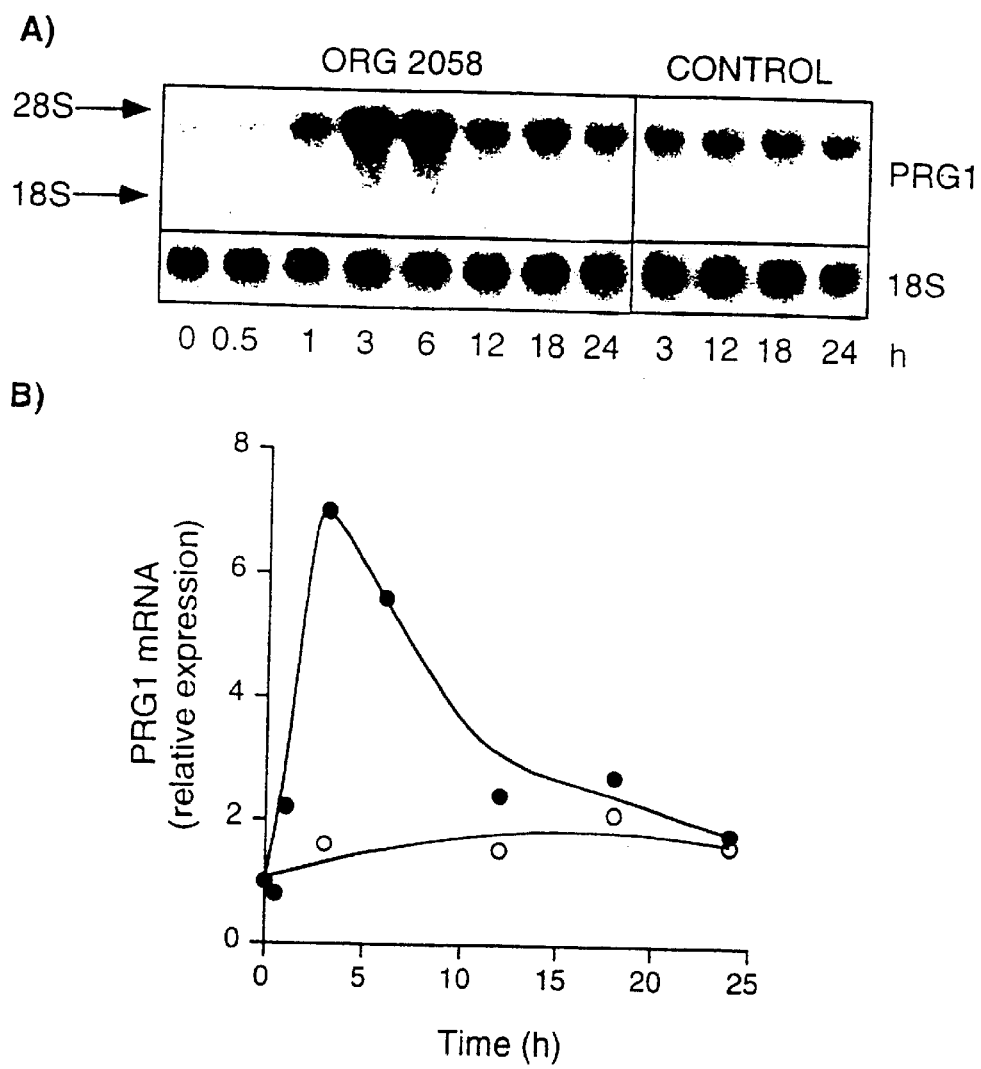
FIG. 5: Regulation of PRG1 mRNA expression by the synthetic progestin ORG 2058.
T-47D cells proliferating in insulin-supplemented serum-free medium were treated with 10 nM ORG 2058 (closed circles) or ethanol vehicle (open circles) and total RNA was harvested for Northern analysis. The Northern blot shown in panel A was probed with a 1.8 kb cDNA sub-clone of PRG1 and with an oligonucleotide complementary to 18S rRNA as a control for loading. Positions of the 28S and 18S ribosomal bands are indicated. Values in panel B were obtained by densitometric analysis of the autoradiograph and are expressed relative to control at 0 h.

To examine in detail the kinetics of progestin induction of PRG1, regulation of PRG1 mRNA expression was investigated in T-47D cells cultured in insulin-supplemented serum-free medium and harvested for mRNA at various time points following ORG 2058 treatment (FIG. 5). PRG1 detected a single mRNA species of approximately 4.4 kb in cells cultured in the absence of ORG 2058. The induction of PRG1 MRNA by ORG 2058 was an early and transient event. Maximal levels of PRG1 induction, 4.4-fold relative to time-matched control in the experiment shown in FIG. 5, were observed at 3 h. following treatment. The induction at 3 h. was typically between 2 and 4.4-fold relative to time-matched controls. After 6 h. mRNA levels had decreased and by 12 h. had returned to control levels. A more detailed analysis of early time-points showed that maximal levels were reached by 2 h. and sustained until 4 h. (data not shown). The increase in PRG1 preceded increases in the proportion of cells in S phase (data not shown), which typically occur around 10 h. in this system (6).

Figure 6:
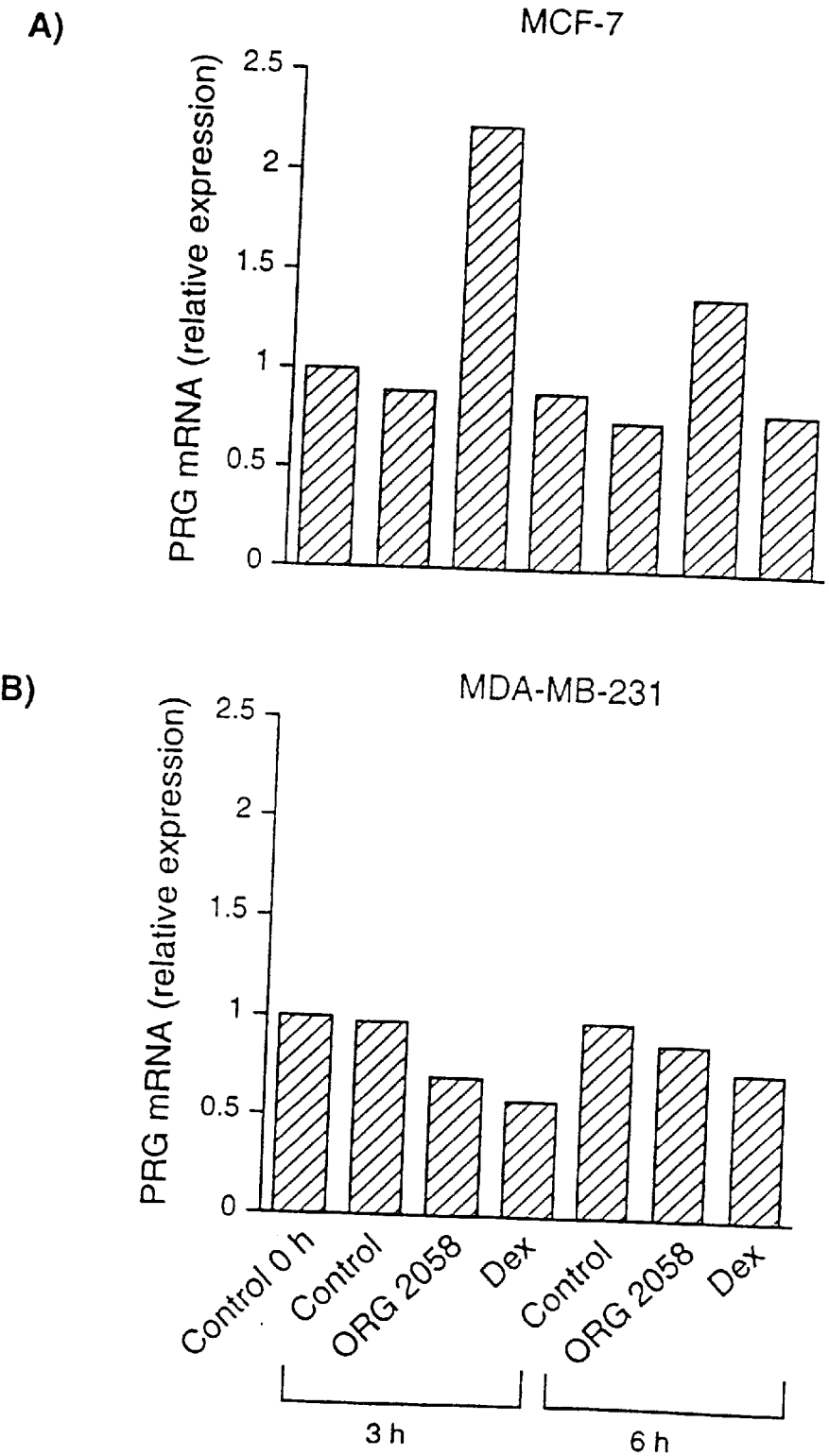
FIG. 6: Regulation of PRG1 mRNA expression in MCF-7 and MDA-MB-231 cells by ORG 2058 and dexamethasone.
MCF-7 (PR + ve, GR + ve) and NIDA-MB-231 (PR–ve, GR+ ve) cells proliferating in RPMI 1640 medium supplemented with 5% fetal calf serum were treated with ORG 2058 (10 nNM), dexamethasone (100 nNM) or ethanol vehicle and harvested for Northern analysis at 3 h. and 6 h. Densitometric analysis of the Northern blot hybridised with 1.8 kb cDNA sub-clone of PRG1 is presented expressed relative to control at 0 h, and adjusted for loading. The data in Panel B were obtained from the mean of two experiments.

Induction of PRG1 mRNA in Breast Cancer Cell Lines is Mediated Via the Progesterone Receptor To determine whether the effects of ORG 2058 on PRG1 expression were likely to be mediated by the PR we examined the effects of other synthetic progestins and the antiprogestin RU 486 in a variety of breast cancer cell lines. T-47D cells, growing exponentially in medium containing 5% FCS. were treated in parallel with the synthetic ORG 2058, R5020 and MPA at 10 nM and harvested for mRNA at 3 h. All 3 synthetic progestins induced PRG1 mRNA between 2- and 2.5-fold above control levels (data not shown). PRG1 mRNA was also induced by the synthetic progestin livial (10 nM) in T-47D cells growing in the presence of 5% charcoal-treated FCS as discussed later. The effect of ORG 2058 on PRG1 mRNA in another PR-positive cell line (MCF-7) and in a PR-negative cell line (MDA MB-231) were investigated. ORG 2058 increased PRG1 mRNA in MCF-7 cells approximately 2-fold above control mRNA levels at 3 h. (FIG. 6A). In contrast in MDA-NB-231 cells the levels of PRG1 mRNA in the presence of ORG 2058 were decreased approximately 30% below control MnRNA levels at 3 h. with recovery at 6 h. (FIG. 6B).

Figure 7:
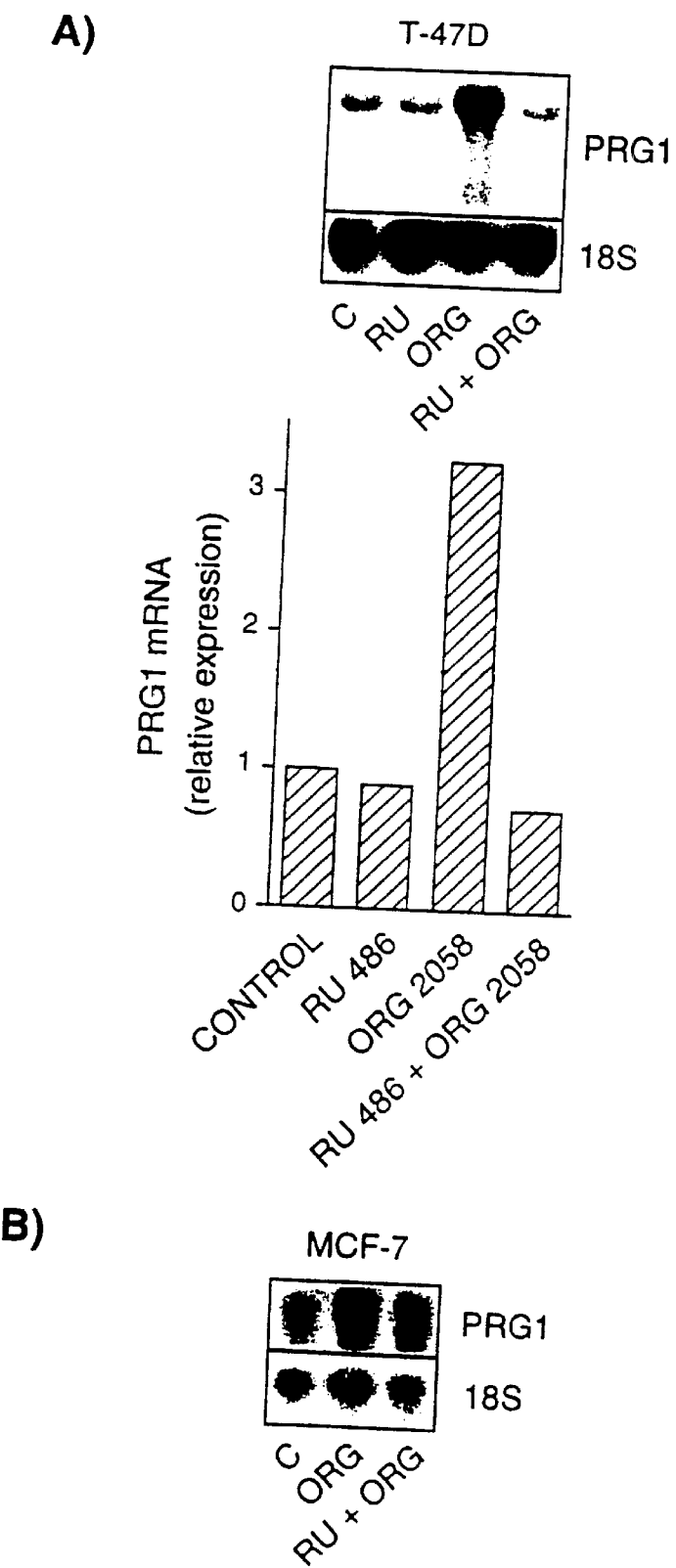
FIG. 7: Antagonism of ORG 2058 induction of PRG1 mRNA by the antiprogestin RU 486.
A) T-47D cells proliferating in insulin-supplemented serum-free medium were treated with ORG 2058 (10 nM), RU 486 (100 nM), the two compounds simultaneously (ORG 2058 + RU 486) or ethanol vehicle and harvested for Northern analysis at 3 h. The Northern blot was probed with the PIG1 fragment of PRG1 and with an oligonucleotide complementary to 18S rRNA as a control for loading. The graph represents densitometric analysis of the autoradiograph expressed relative to control at 3 h.
B) MCF-7 cells proliferating in medium supplemented with 5% FCS were treated with ORG 2058 (10nM). ORG 2058 + RU 486 (100 nM) simultaneously or ethanol vehicle and harvested from Northern analysis at 3 h. The Northern blot was probed with a 1.8 kb cDNA sub-clone of PRG1 and with an oligonucleotide complementary to 18S rRNA as a control for loading.

Additional evidence for the involvement of PR in mediating progestin effects on PRG1 was obtained using the progestin antagonist RU 486. This compound acts as a competitive inhibitor of the binding of progestins to the PR (46) and its effect on the induction of PRG1 mRNA was investigated by treatment of T-47D cells with ORG 2058 (10 nM) and RU 486 (100 nM) either alone or simultaneously in serum-free medium supplemented with insulin. The cells were harvested 3 h. after the treatment, when PRG1 MRNA levels were at a maximum. Simultaneous administration of ORG 2058 and RU 486 led to complete inhibition of progestin-induced PRG1 expression, while treatment with RU 486 alone had no effect on mRNA levels (FIG. 7A). Similar effects were seen in MCF-7 cells grown in the presence of serum although the abrogating effect of RU 486 was not quite as pronounced (FIG. 7B).

Given that the consensus sequence for the glucocorticoid and progesterone response elements is similar (47) one might expect that glucocorticoids could regulate PRG1 expression via the glucocorticoid receptor (GR). To investigate this possibility to GR-positive cell lines. MCF-7 and MDA MB-231, were treated with the synthetic glucocorticoid dexamethasone (100 nM) and harvested at 3 and 6 h. following treatment. No increase in PRG1 mRNA was observed at these times (FIGS. 6A and 6B). Similarly, no increase in PRG1 mRNA was observed in T-47D cells, which also express GR, following treatment with dexamethasone for 3 h. (results not shown). In MDA-MB-231 cells, however, dexamethasone reduced PRG1 mRNA to approximately 60% of control levels at 3 h. with some recovery evident at 6 h. These data are consistent with the progestin effect being mediated via the PR.

PRG1 Induction by Progestin Does Not Require de novo Protein Synthesis

Figure 8:
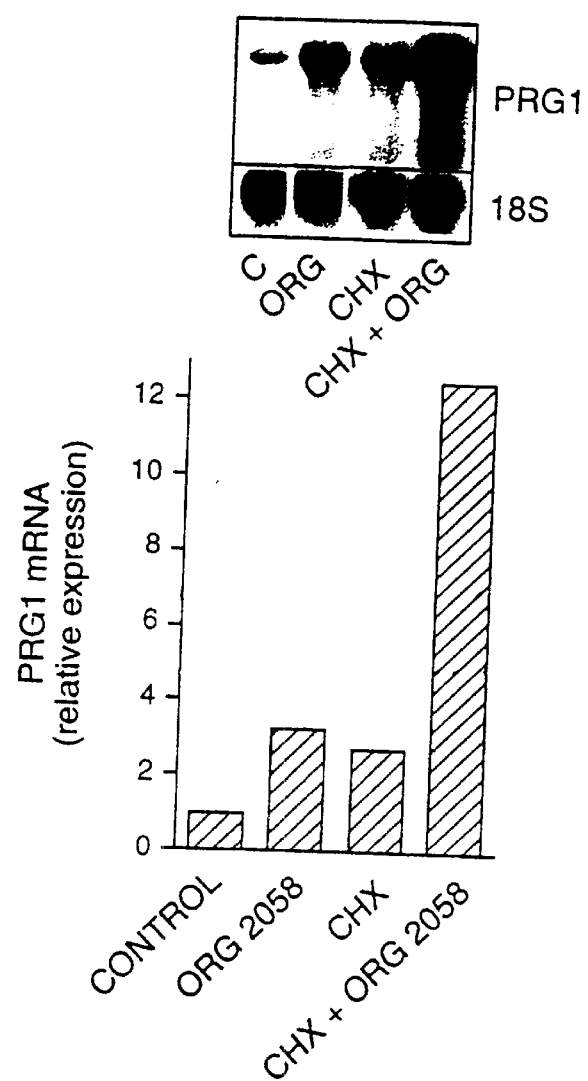
FIG. 8: Effect of the protein synthesis inhibitor cycloheximide on ORG 2058 induction of PRG1 mRNA.
A) T-47D cells proliferating in insulin-supplemented serum-free medium were treated with ORG 2058 (10 nM), cycloheximide (CHX, 20 µg/ml), ORG 2058 and CHX simultaneously or ethanol vehicle and harvested for Northern analysis at 3 h. The Northern blot was probed with the PIG1 fragment of PRG1 and with an oligonucleotide complementary to 18S rRNA as a control for loading. The graph represents densitometric analysis of the autoradiograph expressed relative to control at 3 h.
Figure 8:
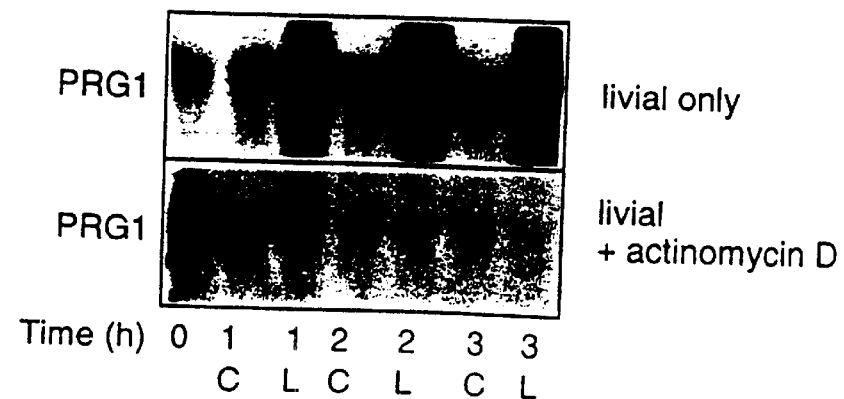

To distinguish between direct activation of PRG1 transcription by the PR or indirect activation via the synthesis of intermediary proteins, T-47D cells were treated with ORG 2058 (10 nM) in the presence of the protein synthesis inhibitor, cycloheximide (20 μg/ml). Cycloheximide failed to block the progestin-mediated induction of PRG1 mRNA. Treatment with cycloheximide alone resulted in an increase of PRG1 mRNA to a level similar to that achieved by ORG 2058 alone, while in the presence of both ORG 2058 and cycloheximide there was "superinduction" of PRG1 mRNA (FIG. 8A). The magnitude of this induction, 12-fold in the experiment shown in FIG. 8. was larger than expected from a combination of the responses to the individual compounds. Such superinduction involving protein synthesis inhibitors is characteristic of genes such as β- and γ-actin, c-fos and c-myc which are switched on early (0–2 h.) following stimulation of cells by mitogens (48–50). Cycloheximide has stabilising effects on mRNA (51), prolongs transcription (48) and can itself act as a nuclear signalling agonist (52) all of which can contribute to the superinduction effect. PRG1 mRNA was not induced in T-47D cells treated with the synthetic progestin livial (10 nM) in the presence of the transcription inhibitor actinomycin D (5 μg/ml) (FIG. 8B). Together these data suggest that the induction of PRG1 mRNA is due to the direct action of the PR on PRG1 transcription and does not require de novo protein synthesis.

Regulation of PRG1 Expression by Breast Cancer Cell Mitogens

Given that expression of rat F-type PFK-2/FBPase-2 is linked to the proliferation state of cells (53) and PRG1 mRNA levels increase prior to the progestin-induced increases in S phase cells, the effect of other known breast cancer cell mitogens on PRG1 expression was examined. T-47D cells were growth-arrested in $G_1$ phase by serum deprivation and stimulated to re-initiate cell cycle progression with insulin, heregulin or basic fibroblast growth factor. These mitogens stimulate cell cycle progression with increases in the S phase population first evident around 12–15 h. and maximal at about 24 h. (32, 54). The induction of PRG1 mRNA due to insulin, heregulin and bFGF were 2.8-, 2.6- and 1.9-fold, respectively at 3 or 4 h. (FIG. 9A). Heregulin has previously been reported to be one of the most potent mitogens for T-47D cells (32) whereas insulin and bFGF are equipotent (54) and therefore the degree of induction of PRG1 mRNA was unrelated to the potency of the mitogens in stimulating cell cycle progression. The regulation of PRG1 mRNA expression by estrogen was examined in MCF-7 breast cancer cells using a model in which cells cultured in serum were growth-arrested in the $G_1$ phase of the cycle by the antiestrogen ICI 182780 and then stimulated to re-enter the cell cycle with 17β-estradiol (30). In this system increases in S phase begin around 12 h. and are maximal between 21 and 24 h. Induction of PRG1 mRNA (2.0-fold) was observed at 4 h. (FIG. 9B). A comparison was also made between T-47D cells growth-arrested by serum deprivation and cells exponentially growing in medium supplemented with 10% fetal calf serum. PRG1 mRNA was detected at very low levels in growth-arrested T-47D cells in unsupplemented serum-free medium while cells cultured in the presence of serum expressed PRG1 mRNA at a 10.9-fold higher level (FIG. 9C). Therefore induction of PRG1 mRNA is not restricted to progestins, but is a common response to mitogenic stimulation. (Also refer to Table 1).

TABLE 1

PRG1 mRNA regulation by breast cancer cell mitogens

| Cell type and treatment | Relative mRNA Expression |
| --- | --- |
| T-47D | |
| Exponentially growing cells¶ | 10.9¶ |
| Insulin (1.7 μM) | 2.8† at 4 h |
| Heregulin (5 nM) | 1.9† at 4 h |
| bFGF (55 pM) | 2.6† at 3 h |
| MCF-7 | |
| 17β estradiol (100 nM) | 2.0‡ at 4 h |

¶Cells were growing exponentially in medium containing 10% fetal calf serum.
†T-47D cells were treated as described in Materials and Methods. PRG1 mRNA levels are expressed relative to levels in cells maintained in serum-free medium.
‡MCF-7 cells were rescued with 17β estradiol following pre-treatment with the antiestrogen ICI 182 780 for 48 h as described in Materials and Methods. PRG1 mRNA is expressed relative to antiestrogen treated control levels.

Production of Bacterially Expressed PRG1 as a FLAG Fusion Protein.

PRG1 was produced as a soluble protein in bacteria in the form of a FLAG fusion protein as described in the Materials and Methods. FIG. 10 shows the results of affinity purification on an anti-FLAG M2 affinity column. The presence of the fusion protein has been detected by SDS-PAGE of fractions and Western blotting with an anti-FLAG antibody. Unpurified bacterial lysate (soluble fraction) (ie the material loaded onto the affinity purification column) is run in lane 2 and a large band at the predicted molecular weight of 6 kDa is present, with several minor lower molecular weight species present that are also antibody-reactive. Following washing (lanes 7–9), glycine was used to elute the fusion protein which was present in fractions 1–6 (lanes 10–15) at the expected molecular weight. Coomassie staining of this gel (not shown) suggests the majority of the fusion protein eluted in lanes 12 and 13 in a substantially pure form.

Summary and Conclusions

The progestin regulation of PRG1 mRNA was studied in some detail and Northern analysis of PRG1 mRNA levels over a 24 h. time period showed a rapid and transient induction by ORG 2058 that peaked at 3 h. and returned to control levels by 12 h. Several lines of evidence are consistent with the view that this response is mediated by the PR. First, the induction of PRG1 mRNA occurred in the presence of three other synthetic progestins, R5020, MPA and livial. Second, although these progestins potentially have some cross-reactivity with the GR (55. 56) the progestin induction does not appear to be mediated by this receptor and the glucocorticoid response element (GRE) as the glucocorticoid dexamethasone had no effect on PRG1 mRNA in T-47D or MCF-7 cell lines. Third, the progestin antagonist, RU 486. inhibited the progestin-induction of PRG1 mRNA. Interestingly, in cells expressing high levels of GR, i.e. MDA-MB-231 cells (44), dexamethasone and ORG 2058 caused a small but significant decrease in PRG1 mRNA levels. The mechanism by which this occurs is not known at this stage but may involve cross-reactivity of ORG 2058 with the GR which in this cell line is able to weakly down-regulate PRG1 mRNA expression.

The progestin induction of PRG1 mRNA is not prevented by the presence of the protein synthesis inhibitor cycloheximide but is blocked by the transcription inhibitor actinomycin D. This strongly suggests that induction of PRG1 by progestin is a direct transcriptional effect of ligand-activated PR on a putative PRE located in the PRG1 gene. A computer search of DNA sequence from the cosmid clone CRI-JC2015 encompassing 3000 bp from the initiating methionine in a 5' direction for an optimal PRE sequence as determined by in vitro studies (57) revealed several PRE-like sequences.

Figure 4:
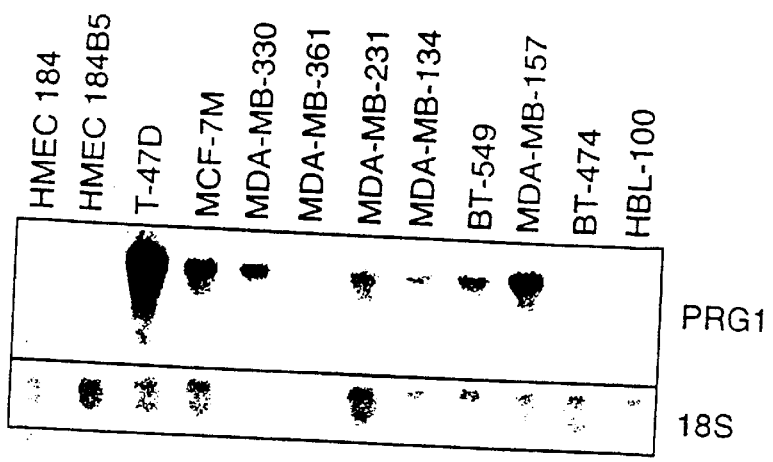
FIG. 4: Expression of PRG1 mRNA in different human tissues and breast cancer and normal breast cell lines.
A) Northern blot analysis of total RNA from different human breast cancer and normal breast cell lines. The blot was probed with a 1.8 kb cDNA sub-clone of PRG1 and an oligonucleotide complementary to 18S rRNA as a loading control.
B) Northern blot analysis of poly $A^+$ RNA from human tissues. The blot was hybridized with a 1.8 kb cDNA sub-clone of PRG1. Molecular sizes of markers are indicated. PBL, peripheral blood leukocytes.
Figure 4:
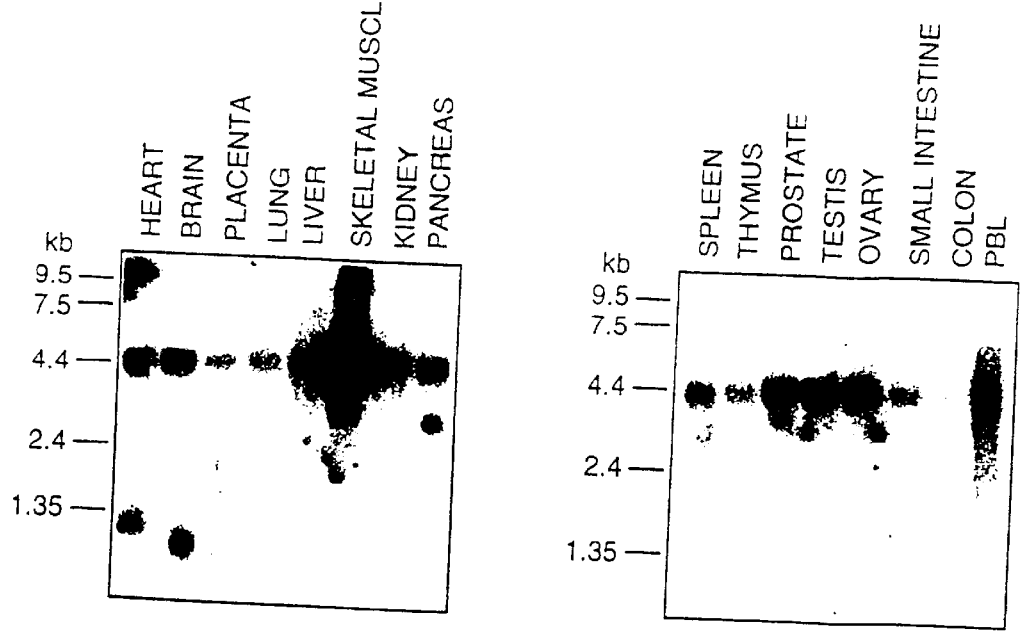

Sequencing of PRG1 shows that PRG1 exhibits significant homology to genes in various species including human that encode the key regulatory bifunctional enzyme phosphofructokinase 2/fructose-2.6-biphosphatase (PFK-2/FBPase-2, EC.2.7.1.105/3.1.3.46) suggesting PRG1 may represent a related enzyme (see FIG. 4). PFK-2/FBPase-2 controls levels of the compound fructose-2,6-bisphosphate (Fru-2,6-P2), which has a major role in the regulation of enzymes controlling glycolysis, gluconeogenesis, and lipogenesis. PRG1 may also control levels of Fru-2,6-$P_2$ or other as yet unidentified regulatory factors.

PRG1 therefore appears to represent a novel gene with potential to be:

(i) one of the few known genes to be directly regulated by progestins and hence an important mediator of progestin action and a marker of clinical responsiveness to progestins; and (ii) a gene involved in cell cycle regulation by progestins and other mitogens and hence a new target for antiproliferative agents.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Clarke C L, Sutherland R L 1990 Progestin regulation of cellular proliferation 11:266–301
2. Shi Y E, Liu Y E, Lippman M E, Dickson R B 1994 Progestins and antiprogestins in mammary tumour growth and metastasis Human Reproduction 9 supplement 1:162–173
3. Lydon J P, DeMayo F J, Funk C R, Mani S K, Hughes A R, Montgomery Jr. C A, Shyamala G, Conneely O M, O'Malley B W 1995 Mice lacking progesterone receptor exhibit pleiotropic reproductive abnormalities Gene Dev 9:2266–2278
4. Anderson T J, Battersby S. King R J B, McPherson K, Going J J 1989 Oral contraceptive use influences resting breast proliferation Hum Pathol 20: 1139–1144
5. Sedlacek S M, Horwitz K B 1984 The role of progestins and progesterone receptors in the treatment of breast cancer Steroids 44:407–84
6. Musgrove E A, Lee C S L, Sutherland R L 1991 Progestins both stimulate and inhibit breast cancer cell cycle progression while increasing expression of transforming growth factor α, epidermal growth factor receptor, c-fos, and c-myc genes Mol Cell Biol 11:5032–5043
7. Alkhalaf M, Murphy L C 1992 Regulation of c-jun and jun-B by progestins T-47D human breast cancer cells Mol Endo 6:1625–1633
8. Murphy L C, Alkhalaf M, Dotzlaw H, Coutts A, Haddad-Alkhalaf B 1994 Regulation of gene expression in T-47D human breast cancer cells by progestins and anti-progestins Human Reproduction 9 supplement 1:174–180
9. Joveux C, Rochefort H, Chalbos D 1989 Progestin increases gene transcription and messenger ribonucleic acid stability of fatty acid synthetase in breast cancer cell Mol Endocrinol 4:681–686
10. Misrahi M, Loosfelt H, Atger M, Merial C, Zerah V, Dessen P, Milgrom E 1988 Organisation of the entire rabbit progesterone receptor mRNA and of the promoter and 5' flanking region of the gene Nucleic Acid Res 16:5459–5472
11. Alexandra I E, Clarke C L, Shine J, Sutherland R L 1989 Progestin inhibition of progesterone receptor gene expression in human breast cancer cells Mol Endocrinol 3:1377–1386
12. Jantzen K, Fritton H P, Igo-Kemenes T, Espel E, Janich S, Cato A C, Mugele K, Beato M 1987 Partial overlapping of binding sequences for steroid hormone receptors and DNaseI hypersensitive sites in the rabbit uteroglobin gene regions Nucleic Acids Res 11:4535–4552
13. Theveny B, Bailly A, Rauch C, Rauch M, Delain E, Milgrom E 1987 Association of DNA bound progesterone receptors Nature 329:79–81
14. Di Lorenzo D, Albetini A, Zava D 1991 Progestin regulation of alkaline phosphatase in the human breast cancer cell line T47D Cancer Res 51:4470–4475
15. Hagley R D, Hissom J R, Moore M R 1987 Progestin stimulation of lactate dehydrogenase in the human breast cancer line T-47D Biochim Biophys Acta 930:167–172
16. Alexandra I E, Shine J, Sutherland R L 1990 Progestin regulation of estrogen receptor messenger RNA in human breast cancer cells Mol Endocrinol 4:821–828
17. Roman S D, Clarke C L, Hall R E, Alexander I E, Sutherland R L 1992 Expression and regulation of retinoic acid receptors in human breast cancer cells Cancer Res 52:2236–2242
18. Murphy L C, Murphy L J, Shiu R P 1988 Progestin regulation of EGF-receptor mRNA accumulation in T-47D human breast cancer cells Biochem Biophys Res Commun 150:192–6
19. Ormandy C J, Graham J, Kelly P A, Clarke C L, Sutherland R L 1992 The effect of progestin on prolactin receptor gene transcription in human breast cancer cells DNA Cell Biol 11:721–726
20. Papa V, Hartmann K K, Rosenthal S M, Maddux B A, Sinteri P K, Goldfine ID 1991 Progestins induce down-regulation of insulin-like growth factor-I (IGF-I) receptors in human breast cancer cells: potential autocrine role of IGF-II Mol Endocrinol 5:709–717
21. Papa V, Reese C C, Brunetti A, Vigneri R, Sinteri P K, Goldfine I D 1990 Progestins increase insulin receptor content and insulin stimulation of growth in human breast carcinoma cells Cancer Res 50:7858–7862
22. Murphy L C, Murphy L J, Dubik D, Bell G I, Shiu, R P 1988 Epidermal growth factor gene expression in human breast cancer cells: regulation of expression by progestins Cancer Res 48:4555–4560
23. Murphy L C, Dotzlaw H 1989 Regulation of transforming growth factor alpha and transforming growth factor beta messenger ribonucleic acid abundance in T-47D, human breast cancer cells Mol Endocrinol 3: 611–7
24. Gong Y, Anzai Y, Murphy L C, Ballejp G, Holinka C F, Gurpide E, Murphy L J 1991 Transforming growth factor gene expression in human endometrial adenocarcinoma cells: regulation by progestins Cancer Res 51:5476–81
25. Poutanen M, Isomaa V, Kainulainen K, Vihko R 1990 Progestin induction of 17 beta-hydroxysteroid dehydrogenase enzyme protein in the T-47D human breast-cancer cell line Int J Cancer 46:897–901

26. Coutts A, Mlurphy L J, Murphv L C 1994 Expression of insulin-like growth factor binding proteins by T-47D human breast cancer cells: regulation by progestins and antiestrogens Breast Cancer Res Treat 32:153–164

27. Musgrove E A, Hamilton J A, Lee C S L, Sweeney K J E, Watts C K W, Sutherland R L 1993 Growth factor, steroid, and steroid antagonist regulation of cyclin gene expression associated with changes in T-47D human breast cancer cell cycle progression Mol Cell Biol 13:3577–3587

28. Musgrove E A, Lee C S L, Bucklev M F, Sutherland R L 1994 Cyclin D1 induction in breast cancer cells shortens G1 and is sufficient for cells arrested in G1 to complete the cell cycle Proc Natl Acad Sci USA 91:8022–8026

29. Musgrove E A, Sarcevic B, Sutherland R L 1996 Inducible expression of cyclin D1 in T-47D human breast cancer cells is sufficient for Cdk2 activation and pRB hyperphosphornyation J Cell Biochem 60:363–378

30. Prall O W J, Sarcevic B, Musgrove E A, Watts C K W, Sutherland R L 1996 Estrogen regulation of cell cycle progression and cyclin/CDK function in human breast cancer cells submitted 31. Liang P, Pardee A B 1992 Differential display of eukaryotic messenger RNA by means of the polymerase chain reaction Science 257:967–971

32. Fiddes R J, Janes P W, Sanderson G M, Sivertsen S P, Sutherland R L, Daly R J 1995 Heregulin (HRG)-induced mitogenic signalling and cytotoxic activity of a HRG/PE40 ligand toxin in human breast cancer cells Cell Growth Differ 6:1567–1577

33. Buckley M F, Sweeney K J E, Hamilton J A, Sini R L, Manning D L, Nicholson R I, deFazio A, Watts C K, Musgrove E A, Sutherland R L 1993 Expression and amplification of cyclin genes in human breast cancer Oncogene 8:2127–33

34. Musgrove E A, Wakeling A E, Sutherland R L 1989 Points of action of estrogen antagonists and a calmodulin antagonist within the MCF-7 human breast cancer cell cycle Cancer Res 49:2398–2404

35. Liang P, Averboukh L, Kevomarsi K, Sager R, Pardee A B 1992 Differential display and cloning of messenger RNAs from human breast cancer versus mammary epithelial cells Cancer Res 52:6966–6968

36. Zheng C. J, Ma N S-F, Dorman T E, Wang M-T, Braunschweigher K, Soares L, Schuster N M, Rothchild C B, Bowden D W, Torrey D, Keith T P, Moir D T, Mao J-I 1994 Development of 124 sequence-tagged sites and cytogenetic localisation of 217 cosmids for human chromosome 10 Genomics 22:55–67

37. Stryer L 1988 Chapter 5 Flow of Genetic Information, ed. W. H. Freeman and Company, New York, p 110–112

38. Lange A J, Pilkis S J 1990 Sequence of human liver 6-phosphofructo-2-kinase/fructose-2,6-bisphosphatase Nucleic Acids Res 18:3652

39. Ventura F, Ambrosio S, Bartrons R, EI-Maghravi M R, Lange A J, Pilkis S J 1995 Cloning and expression of a catalytic core bovine brain 6-phosphofructo-2-kinase/fructose-2,6-bisphosphatase Biochem Biophys Res Commun 209:1140–1148

40. Sakata J, Uyeda K 1990 Bovine heart fructose 6-phosphate, 2-kinase/fructose 2,6-bisphosphatase: complete amino acid sequence and localisation of phosphorylation sites Proc Natl Acad Sci USA 87:4951–4955

41. Lively M O, EI-Maghrabi M R, Pilkis J, D'Angelo G, Colosia A D, Ciavola J A, Fraser B A, Pilkis S J 1988 Complete amino acid sequence of rat liver 6-phosphfructo-2-kiniase/fructose-2,6-bisphosphatase J Biol Chem 263:839–849

42. Sakata J, Abe Y, Uveda K 1991 Molecular cloning of the DNA and expression and characterisation of rat testes fructose-6-phosphate, 2-kinase: fructose-2,6-bisphosphatase J Biol Chem 266:15764–15770

43. Pilksi S J, Claus T H, Kurland I J, Langer A J 1995 6-phosphofructo-2-kinase/fructose-2,6-bisphosphatase: a metabolic signalling enzyme Annu Rev Biochem 64:799–835

44. Hall R E, Lee C S L, Alexandra I E, Shine J, Clarke C L, Sutherland R S 1990 Steroid hormone receptor gene expression in human breast cancer cells: inverse relationship between oestrogen and glucocorticoid receptor messenger RNA levels Int J Cancer 46:1081–1087

45. Sutherland R L, Hall R E, Pang G Y N, Musgrove E A, Clarker C L 1988 Effect of medroxprogesterone acetate in proliferation and cell cycle kinetics of human mammary carcinoma cells Cancer Res 48:5084–5091

46. Bardon S, Vignon F, Chalbos D, Rochefort H 1985 RU486. A progestin and glucocorticoid antagonist, inhibits the growth of breast cancer cells via the progesterone receptor J Clin Enfocrinol Metab 60:692–697

47. Carson-Jurica M A, Schrader W T, O'Malley B W 1990 Steroid receptor family: structure and functions Endocr Rev 11:201–220

48. Elder P K, Schmidt L J, Ono T, Getz M J 1984 Specific stimulation of actin gene transcription by epidermal growth factor and cycloheximide Proc Natl Acad Sci USA 81:7476–7480

49. Greenberg M E, Ziff E B 1984 Stimulation of 3T3 cells induces transcription of the c-fos proto-oncogene Nature-311:433–438

50. Greenberg M E, Hermanowski A L, Ziff E B 1986 Effect of protein synthesis inhibitors on growth factor activation of c-fos, c-mvs, and actin gene transcription Mol Cell Biol 6:1050–1057

51. Rahmsdorf H J, Schonthal A, Angel P, Litfin M, Ruither U, Herrlich P 1987 Posttranscriptional regulation of c-fos mRNA expression Nucleic Acids Res 15:1643–1659

52. Edwards D R, Mahadevan L C 1992 Protein synthesis inhibitors differentially superinduce c-fos and c-jun by three distinct mechanisms: lack of evidence for labile repressors EMBO J 11:2415–2424

53. Darville M I, Antoine I V, Mertens-Strijthagen J R, Dupriez V J, Rousseau GG 1985 An E2F-dependent late-serum-response promoter in a gene that controls glycolysis Oncogene 11:1509–1517

54. Musgrove E A, Sutherland R L 1993 Acute effects of growth factors on T-47D breast cancer cell cycle progression European Journal of Cancer 29A:2273–2279

55. Poulin R, Baker D, Poirier D, Labrie F 1989 Androgen and glucocorticoid receptor-mediated inhibition of cell proliferation by medroxprogesterone acetate in ZR-75-1 human breast cancer cells Breast Cancer Res Treat 13:161–172

56. Poulin R, Baker D, Poirier D, Labrie F 1990 Multiple actions of synthetic 'progestins' on the growth of ZR-75-1 human breast cancer cells: An in vitro model for the simulations assay of androgen, progestin, estrogen and glucocorticoid agonistic and antagonistic activities of steroids Breast Cancer Res Treat 17:197–210

57. Lieberman B. A., Bona B. J., Edwards D. P., Nordeen S. K., 1993, The Constitution of a progesterone response element. Molecular Endocrinology 7: 515–527.

58. Van Schaftingen, E. et al. 1982, European Journal of Biochemistry 129: 191–195

59. EI-Maghrabi, M. R. et al, 1982, Journal of Biological Chemistry 257: 7603–7607.

What is claimed is:

1. An isolated DNA molecule comprising a nucleotide sequence more than 80% homologous to any one of the nucleotide sequences shown at:
   (i) FIG. 2B (SEQ ID NO:1) from nucleotide 1 to 3018, and
   (ii) FIG. 2B (SEQ ID NO:1) from nucleotide 141 to 3018, wherein said DNA molecule encodes a protein with phosphofructo-2-kinase/fructose-2, 6-biphosphatase activity.

2. A DNA molecule according to claim 1, said DNA molecule being of human origin.

3. The DNA molecule according to claim 2, said DNA molecule being of human kidney cell or breast cancer cell origin or which encodes a protein normally expressed in human kidney cells, breast tissue or tumor cells.

4. An expression vector comprising a DNA molecule according to claim 1.

5. A recombinant host cell including a DNA molecule according to claim 1.

6. An isolated DNA molecule comprising a progestin-regulatory element(s)(PRE) present in the DNA molecule according to claim 1.

7. An isolated DNA molecule comprising a nucleotide sequence more than 90% homologous to any one of the nucleotide sequences shown at:
   (i) FIG. 2B (SEQ ID NO:1) from nucleotide 1 to 3018, and
   (ii) FIG. 2B (SEQ ID NO:1) from nucleotide 141 to 3018, wherein said DNA molecule encodes a protein with phosphofructo-2-kinase/fructose-2, 6-biphosphatase activity.

8. An isolated DNA molecule having the nucleotide sequence shown at FIG. 2B (SEQ ID NO:1) from nucleotide 1 to 3018, wherein said DNA molecule encodes a protein with phosphofructo-2-kinase/fructose-2, 6-biphosphatase activity or a nucleotide sequence complementary thereto.

9. An isolated DNA molecule having the nucleotide sequence shown at FIG. 2B (SEQ ID NO:1) from nucleotide 1 to 470, wherein said DNA molecule encodes a protein with phosphofructo-2-kinase/fructose-2, 6-biphosphatase activity or a nucleotide sequence complementary thereto.

10. An isolated DNA molecule having the nucleotide sequence shown at FIG. 2B (SEQ ID NO:1) from nucleotide 141 to 3018, wherein said DNA molecule encodes a protein with phosphofructo-2-kinase/fructose-2, 6-biphosphatase activity or a nucleotide sequence complementary thereto.

11. An isolated DNA molecule having the nucleotide sequence shown at FIG. 2B (SEQ ID NO:1) from nucleotide 470 to 2103, wherein said DNA molecule encodes a protein with phosphofructo-2-kinase/fructose-2, 6-biphosphatase activity.

12. A polypeptide in a substantially pure form, said polypeptide comprising an amino acid sequence as shown at FIG. 2B (SEQ ID NO:2) or an enzymatic portion thereof, wherein said polypeptide or enzymatic portion thereof has phosphofructo-2-kinase/fructose-2, 6-biphosphatase activity.

13. A polypeptide in a substantially pure form, said polypeptide consisting of an amino acid sequence as shown at FIG. 2B (SEQ ID NO:2) wherein said polypeptide or enzymatic portion thereof has phosphofructo-2-kinase/fructose-2, 6-biphosphatase activity.

\* \* \* \* \*

SEQUENCE LISTING

<160> NUMBER OF SEQ ID NOS: 9

<210> SEQ ID NO 1
<211> LENGTH: 3018
<212> TYPE: DNA
<213> ORGANISM: Homo Sapiens

<400> SEQUENCE: 1

| | | | | | |
|---|---|---|---|---|---|
| caggctgctt | cccggctcgc | ccaccctcct | ccccacgtgg | aaggggggctg | ggacccaagg | 60 |
| aatgcggccc | gccccgaggc | tgacgtacgc | gtctgcggcc | agcccggact | ctttaaaagc | 120 |
| cggcggtgcg | cggggcatcc | cagccaagcc | ggagaggagg | cgagcggcag | ggcctggtgg | 180 |
| cgagagcgcg | gctgtcactg | cgcccgagca | tcccagagct | ttccgagcgg | acgagccggc | 240 |
| cgtgccgggc | atccccagcc | tcgctaccct | cgcagcacac | gtcgagcccc | gcacaggcga | 300 |
| gggtccggaa | cttagcccaa | agcacgtttc | ccctggcagc | gcaggaaacg | cccggccgcg | 360 |
| cgccggcgca | cgcccccctc | tcctcctttg | ttccgggggt | cggcggccgc | tctcctgcca | 420 |
| gcgtcgggat | ctcggccccg | ggaggcgggc | cgtcgggcgc | agccgcgaag | atgccgttgg | 480 |
| aactgacgca | gagccgagtg | cagaagatct | gggtgcccgt | ggaccacagg | ccctcgttgc | 540 |
| ccagatcctg | tgggccaaag | ctgaccaact | cccccaccgt | catcgtcatg | gtgggcctcc | 600 |
| ccgcccgggg | caagacctac | atctccaaga | agctgactcg | ctacctcaac | tggattggcg | 660 |
| tccccacaaa | agtgactgtc | aacgtgggga | gtatcgccgg | gaggctgtga | agcagtacag | 720 |
| ctcctacatt | cttccgcccc | gacaatgagg | aagccatgaa | agtccggaag | caatgtgcct | 780 |
| tagctgcctt | gagagatgtc | aaaagctacc | tggcgaaaga | aggggggacaa | attgcggttt | 840 |
| tcgatgccac | caatactact | agagagagga | gacacatgat | ccttcatttt | gccaaagaaa | 900 |
| atgactttaa | ggcgttttc | atcgagtcgg | tgtgcgacga | ccctacagtt | gtggcctcca | 960 |
| atatcatgga | agttaaaatc | tccagcccgg | attacaaaga | ctgcaactcg | gcagaagcca | 1020 |
| tggacgactt | catgaagagg | atcagttgct | atgaagccag | ctaccagccc | ctcgaccccg | 1080 |
| acaaatgcga | cagggacttg | tcgctgatca | aggtgattga | cgtgggccgg | aggttcctgg | 1140 |
| tgaaccgggt | gcaggaccac | atccagagcc | gcatcgtgta | ctacctgatg | aacatccacg | 1200 |
| tgcagccgcg | taccatctac | ctgtgccggc | acggcgagaa | cgagcacaac | ctccagggcc | 1260 |
| gcatcggggg | cgactcaggc | ctgtccagcc | ggggcaagaa | gtttgccagt | gctctgagca | 1320 |
| agttcgtgga | ggagcagaac | ctgaaggacc | tgcgtgtgga | ccagccagct | gaagagcacc | 1380 |
| atccagacgg | ccgaggcgct | gcgcggctgc | cctacgagca | gtggaaggcg | ctcaatgaga | 1440 |
| tcgacgcggg | cgtctgtgag | gagctgacct | acgaggagat | cagggacacc | taccctgagg | 1500 |
| agtatgcgct | gcgggagcag | gacaagtact | attaccgcta | ccccaccggg | gagtcctacc | 1560 |
| aggacctggt | ccagcgcttg | gagccagtga | tcatggagct | ggagcggcag | gagaatgtgc | 1620 |
| tggtcatctg | ccaccaggcc | gtcctgcgct | gcctgcttgc | ctacttcctg | gataagagtg | 1680 |
| cagaggagat | gccctacctg | aaatgccctc | ttcacaccgt | cctgaaactg | acgcctgtcg | 1740 |
| cttatggctg | ccgtgtggaa | tccatctacc | tgaacgtgga | gtccgtctgc | acacaccggg | 1800 |
| agaggtcaga | ggatgcaaag | aagggaccta | acccgctcat | gagacgcaat | agtgtcaccc | 1860 |
| cgctagccag | ccccgaaccc | accaaaaagc | ctcgcatcaa | cagctttgag | gagcatgtgg | 1920 |
| cctccaccctc | ggccgccctg | cccagctgcc | tgccccggga | ggtgcccacg | cagctgcctg | 1980 |
| gacaaaaacat | gaaaggctcc | cggagcagcg | ctgactcctc | caggaaacac | tgaggcagac | 2040 |

-continued

```
gtgtcggttc cattccattt ccatttctgc agcttagctt gtgtcctgcc ctccgcccga   2100
ggcaaaacgt atcctgagga cttcttccgg agagggtggg gtggagcagc ggggagcct    2160 tggccgaaga gaaccatgct tggcaccgtc tgtgtcccct cggccgctgg acaccagaaa   2220
gccacgtggg tccctggcgc cctgccttta gccgtgggc cctcacctcc acctctgggt   2280
ttcctaggaa tgtccagcct cggagacctt cacaaagcct tgggagggtg atgagtgctg   2340
gtcctgacaa gaggccgctg gggacactgt gctgttttgt ttcgtttctg tgatctcccg   2400
gcacgtttgg agctgggaag accacactgg tggcagaatc ctaaaattaa aggaggcagg   2460
ctcctagttg ctgaaagtta aggaatgtgt aaaacctcca cgtgactgtt tggtgcatct   2520
tgacctggga agacgcctca tgggaacgaa cttggacagg tgttgggttg aggcctcttc   2580
tgcaggaagt ccctgagctg agacgcaagt tggctgggtg gtccacaccc tggctctcct   2640
gcaggtccac acaccttcca ggcctgtggc tgcctccaaa gatgtgcaag ggcaggctgg   2700
ctgcacgggg agagggaagt attttgccga aatatgagaa ctggggcctc ctgctcccag   2760
ggagctccag ggcccctctc tcctcccacc tggacttggg gggaactgag aaacactttc   2820
ctggagctgc tggcttttgc acttttttga tggcagaagt gtgacctgag agtcccacct   2880
tctcttcagg aacgtagatg ttgggtgtc ttgccctggg gggcttggaa cctctgaagg   2940
tggggagcgg aacacctggc atccttcccc agcacttgca ttaccgtccc tgctcttccc   3000
aggtggggac ccggaatt                                                 3018
```

<210> SEQ ID NO 2
<211> LENGTH: 520
<212> TYPE: PRT
<213> ORGANISM: Homo sapiens

<400> SEQUENCE: 2

```
Met Pro Leu Glu Leu Thr Gln Ser Arg Val Gln Lys Ile Trp Val Pro
  1               5                  10                  15

Val Asp His Arg Pro Ser Leu Pro Arg Ser Cys Gly Pro Lys Leu Thr
             20                  25                  30

Asn Ser Pro Thr Val Ile Val Met Val Gly Leu Pro Ala Arg Gly Lys
         35                  40                  45

Thr Tyr Ile Ser Lys Lys Leu Thr Arg Tyr Leu Asn Trp Ile Gly Val
     50                  55                  60

Pro Thr Lys Val Phe Asn Val Gly Glu Tyr Arg Arg Glu Ala Val Lys
 65                  70                  75                  80

Gln Tyr Ser Ser Tyr Asn Phe Phe Arg Pro Asp Asn Glu Glu Ala Met
                 85                  90                  95

Lys Val Arg Lys Gln Cys Ala Leu Ala Ala Leu Arg Asp Val Lys Ser
            100                 105                 110

Tyr Leu Ala Lys Glu Gly Gly Gln Ile Ala Val Phe Asp Ala Thr Asn
        115                 120                 125

Thr Thr Arg Glu Arg Arg His Met Ile Leu His Phe Ala Lys Glu Asn
    130                 135                 140

Asp Phe Lys Ala Phe Phe Ile Glu Ser Val Cys Asp Asp Pro Thr Val
145                 150                 155                 160

Val Ala Ser Asn Ile Met Glu Val Lys Ile Ser Ser Pro Asp Tyr Lys
                165                 170                 175

Asp Cys Asn Ser Ala Glu Ala Met Asp Asp Phe Met Lys Arg Ile Ser
            180                 185                 190
```

-continued

```
Cys Tyr Glu Ala Ser Tyr Gln Pro Leu Asp Pro Asp Lys Cys Asp Arg
            195                 200                 205
Asp Leu Ser Leu Ile Lys Val Ile Asp Val Gly Arg Arg Phe Leu Val
            210                 215                 220
Asn Arg Val Gln Asp His Ile Gln Ser Arg Ile Val Tyr Tyr Leu Met
225                 230                 235                 240
Asn Ile His Val Gln Pro Arg Thr Ile Tyr Leu Cys Arg His Gly Glu
                245                 250                 255
Asn Glu His Asn Leu Gln Gly Arg Ile Gly Gly Asp Ser Gly Leu Ser
                260                 265                 270
Ser Arg Gly Lys Lys Phe Ala Ser Ala Leu Ser Lys Phe Val Glu Glu
            275                 280                 285
Gln Asn Leu Lys Asp Leu Arg Val Trp Thr Ser Gln Leu Lys Ser Thr
            290                 295                 300
Ile Gln Thr Ala Glu Ala Leu Arg Leu Pro Tyr Glu Gln Trp Lys Ala
305                 310                 315                 320
Leu Asn Glu Ile Asp Ala Gly Val Cys Glu Glu Leu Thr Tyr Glu Glu
                325                 330                 335
Ile Arg Asp Thr Tyr Pro Glu Glu Tyr Ala Leu Arg Glu Gln Asp Lys
                340                 345                 350
Tyr Tyr Tyr Arg Tyr Pro Thr Gly Glu Ser Tyr Gln Asp Leu Val Gln
            355                 360                 365
Arg Leu Glu Pro Val Ile Met Glu Leu Glu Arg Gln Glu Asn Val Leu
            370                 375                 380
Val Ile Cys His Gln Ala Val Leu Arg Cys Leu Leu Ala Tyr Phe Leu
385                 390                 395                 400
Asp Lys Ser Ala Glu Met Pro Tyr Leu Lys Cys Pro Leu His Thr
                405                 410                 415
Val Leu Lys Leu Thr Pro Val Ala Tyr Gly Cys Arg Val Glu Ser Ile
                420                 425                 430
Tyr Leu Asn Val Glu Ser Val Cys Thr His Arg Glu Arg Ser Glu Asp
            435                 440                 445
Ala Lys Lys Gly Pro Asn Pro Leu Met Arg Arg Asn Ser Val Thr Pro
            450                 455                 460
Leu Ala Ser Pro Glu Pro Thr Lys Lys Pro Arg Ile Asn Ser Phe Glu
465                 470                 475                 480
Glu His Val Ala Ser Thr Ser Ala Ala Leu Pro Ser Cys Leu Pro Pro
                485                 490                 495
Glu Val Pro Thr Gln Leu Pro Gly Gln Asn Met Lys Gly Ser Arg Ser
                500                 505                 510
Ser Ala Asp Ser Ser Arg Lys His
            515                 520

<210> SEQ ID NO 3
<211> LENGTH: 10
<212> TYPE: DNA
<213> ORGANISM: Artificial Sequence
<220> FEATURE:
<223> OTHER INFORMATION: Oligonucleotide primer for differential
      display

<400> SEQUENCE: 3
caaacgtcgg                                                            10

<210> SEQ ID NO 4
<211> LENGTH: 32
```

-continued

```
<212> TYPE: DNA
<213> ORGANISM: Artificial Sequence
<220> FEATURE:
<223> OTHER INFORMATION: PCR oligonucleotide primer

<400> SEQUENCE: 4
atgaattcat gccgttggaa ctgacgcaga gc                                    32

<210> SEQ ID NO 5
<211> LENGTH: 36
<212> TYPE: DNA
<213> ORGANISM: Artificial Sequence
<220> FEATURE:
<223> OTHER INFORMATION: PCR oligonucleotide primer

<400> SEQUENCE: 5
tacctagtcg actcagtgtt tcctggagga gtcagc                                36

<210> SEQ ID NO 6
<211> LENGTH: 21
<212> TYPE: DNA
<213> ORGANISM: Homo Sapiens

<400> SEQUENCE: 6
accgtcatcg tcatcggtgg g                                                21

<210> SEQ ID NO 7
<211> LENGTH: 471
<212> TYPE: PRT
<213> ORGANISM: Homo Sapien

<400> SEQUENCE: 7
```

Met Ser Pro Glu Met Gly Glu Leu Thr Gln Thr Arg Leu Gln Lys Ile
1               5                   10                  15

Trp Ile Pro His Ser Gly Ser Ser Arg Leu Gln Arg Arg Gly
            20                  25                  30

Ser Ser Ile Pro Gln Phe Thr Asn Ser Pro Thr Met Val Ile Met Val
        35                  40                  45

Gly Leu Pro Ala Arg Gly Lys Thr Tyr Ile Ser Thr Lys Leu Thr Arg
    50                  55                  60

Tyr Leu Asn Trp Ile Gly Thr Pro Thr Lys Val Phe Asn Leu Gly Gln
65                  70                  75                  80

Tyr Arg Arg Glu Ala Val Ser Tyr Lys Asn Tyr Glu Phe Phe Leu Pro
                85                  90                  95

Asp Asn Met Glu Ala Leu Gln Ile Arg Lys Gln Cys Ala Leu Ala Ala
            100                 105                 110

Leu Lys Asp Val His Asn Tyr Leu Ser His Glu Glu Gly His Val Ala
        115                 120                 125

Val Phe Asp Ala Thr Asn Thr Thr Arg Glu Arg Arg Ser Leu Ile Leu
    130                 135                 140

Gln Phe Ala Lys Glu His Gly Tyr Lys Val Phe Phe Ile Glu Ser Ile
145                 150                 155                 160

Cys Asn Asp Pro Gly Ile Ile Ala Glu Asn Ile Arg Gln Val Lys Leu
                165                 170                 175

Gly Ser Pro Asp Tyr Ile Asp Cys Asp Arg Glu Lys Val Leu Glu Asp
            180                 185                 190

Phe Leu Lys Arg Ile Glu Cys Tyr Glu Val Asn Tyr Gln Pro Leu Asp
        195                 200                 205

Glu Glu Leu Asp Ser His Leu Ser Tyr Ile Lys Ile Phe Asp Val Gly

-continued

```
                210                 215                 220
Thr Arg Tyr Met Val Asn Arg Val Gln Asp His Ile Gln Ser Arg Thr
225                 230                 235                 240

Val Tyr Tyr Leu Met Asn Ile His Val Thr Pro Arg Ser Ile Tyr Leu
                245                 250                 255

Cys Arg His Gly Glu Ser Glu Leu Asn Ile Arg Gly Glu Ile Gly Gly
                260                 265                 270

Asp Ser Gly Leu Ser Val Arg Gly Lys Gln Tyr Ala Tyr Ala Leu Ala
                275                 280                 285

Asn Phe Ile Gln Ser Gln Gly Ile Ser Ser Leu Lys Val Trp Thr Ser
                290                 295                 300

Arg Met Lys Arg Thr Ile Gln Thr Ala Glu Ala Leu Gly Val Pro Tyr
305                 310                 315                 320

Glu Gln Trp Lys Ala Leu Asn Glu Ile Asp Ala Gly Val Cys Glu Glu
                325                 330                 335

Met Thr Tyr Glu Glu Ile Gln Glu His Tyr Pro Glu Glu Phe Ala Leu
                340                 345                 350

Arg Asp Gln Asp Lys Tyr Arg Tyr Arg Tyr Pro Lys Gly Glu Ser Tyr
                355                 360                 365

Glu Asp Leu Val Gln Arg Leu Glu Pro Val Ile Met Glu Leu Glu Arg
370                 375                 380

Gln Glu Asn Val Leu Val Ile Cys His Gln Ala Val Met Arg Cys Leu
385                 390                 395                 400

Leu Ala Tyr Phe Leu Asp Lys Ser Ser Asp Glu Leu Pro Tyr Leu Lys
                405                 410                 415

Cys Pro Leu His Thr Val Leu Lys Leu Thr Pro Val Ala Tyr Gly Cys
                420                 425                 430

Lys Val Glu Ser Ile Tyr Leu Asn Val Glu Ala Val Asn Thr His Arg
                435                 440                 445

Glu Lys Pro Glu Asn Val Asp Ile Thr Arg Glu Pro Glu Glu Ala Leu
                450                 455                 460

Asp Thr Val Pro Ala His Tyr
465                 470

<210> SEQ ID NO 8
<211> LENGTH: 476
<212> TYPE: PRT
<213> ORGANISM: Bos taurus

<400> SEQUENCE: 8

Ser Glu Gly Val Glu Gly Arg Ala Ser Arg Gly Lys Met Pro Leu
1               5                   10                  15

Glu Leu Thr Gln Ser Arg Val Gln Lys Ile Trp Ile Pro Val Asp His
                20                  25                  30

Arg Pro Ser Leu Pro Arg Thr Cys Gly Pro Lys Leu Thr Asn Ser Pro
                35                  40                  45

Thr Val Ile Val Met Val Gly Leu Pro Ala Arg Gly Lys Thr Tyr Ile
                50                  55                  60

Ser Lys Lys Leu Thr Arg Tyr Leu Asn Trp Ile Gly Val Pro Thr Lys
65                  70                  75                  80

Val Phe Asn Leu Gly Glu Tyr Arg Arg Asp Gly Val Lys Gln Tyr Ser
                85                  90                  95

Ser Tyr Asn Phe Phe Arg Pro Asp Asn Glu Glu Ala Met Lys Val Arg
                100                 105                 110
```

```
Lys Gln Cys Ala Leu Ala Ala Leu Arg Asp Val Lys Ser Tyr Leu Thr
            115                 120                 125

Lys Glu Gly Gly Gln Ile Ala Val Phe Asp Ala Thr Asn Thr Thr Arg
        130                 135                 140

Glu Arg Arg His Met Ile Leu His Phe Pro Lys Glu Asn Asp Phe Lys
145                 150                 155                 160

Val Phe Phe Ile Glu Ser Val Cys Asp Asp Pro Thr Val Val Ala Ser
                165                 170                 175

Asn Ile Met Glu Val Lys Ile Ser Ser Pro Asp Tyr Lys Asp Cys Asn
            180                 185                 190

Ser Arg Glu Asn Ala Met Asp Asp Phe Met Lys Arg Ile Asn Cys Tyr
        195                 200                 205

Glu Ala Ser Tyr Gln Pro Leu Asp Pro Asp Asn Asp Arg Asp Leu
210                 215                 220

Ser Leu Ile Lys Val Ile Asp Val Gly Gln Arg Phe Leu Val Asn Arg
225                 230                 235                 240

Val Gln Asp His Ile Gln Arg Arg Ile Val Tyr Tyr Leu Met Asn Ile
                245                 250                 255

His Trp Gln Pro Arg Thr Ile Tyr Leu Cys Arg His Gly Glu Ser Lys
            260                 265                 270

His Asn Leu Gln Gly Lys Ile Gly Gly Asp Ser Gly Leu Ser Ser Arg
        275                 280                 285

Gly Arg Lys Phe Ala Asn Ala Leu Ser Lys Phe Val Glu Glu Gln Asn
290                 295                 300

Leu Lys Asp Leu Lys Val Trp Thr Ser Gln Leu Lys Ser Thr Ile Gln
305                 310                 315                 320

Thr Ala Glu Ala Leu Gln Leu Pro Tyr Glu Gln Trp Lys Ala Leu Asn
                325                 330                 335

Glu Ile Asp Ala Gly Val Cys Glu Glu Met Thr Tyr Glu Glu Ile Lys
            340                 345                 350

Asp Thr Tyr Pro Glu Glu Tyr Ala Leu Ala Glu Ala Asp Lys Tyr Tyr
        355                 360                 365

Tyr Arg Tyr Pro Thr Gly Glu Ser Tyr Gln Asp Leu Val Gln Arg Leu
370                 375                 380

Glu Pro Val Ile Met Glu Leu Glu Arg Gln Glu Asn Val Leu Val Ile
385                 390                 395                 400

Cys His Gln Ala Val Cys Val Cys Leu Leu Ala Tyr Phe Leu Asp Lys
                405                 410                 415

Ser Ala Glu Glu Met Pro Tyr Leu Lys Cys Pro Leu His Ala Val Leu
            420                 425                 430

Lys Leu Thr Pro Ile Ala Tyr Gly Cys Arg Val Glu Ser Ile Tyr Leu
        435                 440                 445

Asn Val Glu Ser Val Ser Thr His Arg Glu Arg Ser Glu Asp Ala Lys
450                 455                 460

Lys Gly Pro Asn Pro Leu Met Arg Ser Asn Ser His
465                 470                 475
```

<210> SEQ ID NO 9
<211> LENGTH: 531
<212> TYPE: PRT
<213> ORGANISM: Bos taurus

<400> SEQUENCE: 9

```
Met Ser Gly Asn Pro Ala Ser Ser Ser Glu Gln Asn Asn Asn Ser Tyr
  1               5                  10                  15
```

-continued

Glu Thr Lys Ala Ser Leu Arg Ile Ser Glu Lys Lys Cys Ser Trp Ala
            20                  25                  30

Ser Tyr Met Thr Asn Ser Pro Thr Leu Ile Val Met Ile Gly Leu Pro
            35                  40                  45

Ala Arg Gly Lys Thr Tyr Val Ser Lys Lys Leu Thr Arg Tyr Leu Asn
        50                  55                  60

Trp Ile Gly Val Pro Thr Lys Val Phe Asn Leu Gly Val Tyr Arg Arg
65                  70                  75                  80

Gln Ala Val Lys Ser Tyr Lys Ser Tyr Asp Phe Phe Arg His Asp Asn
                85                  90                  95

Glu Glu Ala Met Lys Ile Arg Lys Gln Cys Ala Leu Val Ala Leu Lys
            100                 105                 110

Asp Val Lys Ala Tyr Leu Thr Glu Glu Ser Gly Gln Ile Ala Val Phe
            115                 120                 125

Asp Ala Thr Asn Thr Thr Arg Glu Arg Arg Asp Leu Ile Leu Asn Phe
            130                 135                 140

Ala Glu Glu Asn Ser Phe Lys Val Phe Val Glu Ser Val Cys Asp
145                 150                 155                 160

Asp Pro Asp Val Ile Ala Ala Asn Ile Leu Glu Val Lys Val Ser Ser
                165                 170                 175

Pro Asp Tyr Pro Glu Arg Asn Arg Glu Asn Val Met Asp Asp Phe Leu
            180                 185                 190

Lys Arg Ile Glu Cys Tyr Lys Val Thr Tyr Gln Pro Leu Asp Pro Asp
            195                 200                 205

Ser His Asp Lys Asp Leu Ser Phe Ile Lys Val Ile Asn Val Gly Gln
        210                 215                 220

Arg Phe Leu Val Asn Lys Val Gln Asp Tyr Ile Gln Ser Lys Ile Val
225                 230                 235                 240

Tyr Tyr Leu Met Asn Ile His Val His Pro Arg Thr Ile Tyr Leu Cys
                245                 250                 255

Arg His Gly Glu Ser Glu Phe Asn Leu Leu Gly Lys Ile Gly Gly Asp
            260                 265                 270

Ser Gly Leu Ser Val Arg Gly Lys Gln Phe Ala Gln Ala Leu Arg Lys
        275                 280                 285

Phe Leu Glu Glu Gln Glu Ile Ala Asp Leu Lys Val Trp Thr Ser Gln
290                 295                 300

Leu Lys Arg Thr Ile Gln Thr Ala Glu Ser Leu Gly Val Thr Tyr Glu
305                 310                 315                 320

Gln Trp Lys Ile Leu Asn Glu Ile Asp Ala Gly Val Cys Glu Glu Met
            325                 330                 335

Thr Tyr Ala Glu Ile Gln Glu Gln Tyr Pro Asp Glu Phe Ala Leu Arg
            340                 345                 350

Asp Glu Glu Lys Tyr Leu Tyr Arg Tyr Pro Gly Gly Glu Ser Tyr Gln
            355                 360                 365

Asp Leu Val Gln Arg Leu Glu Pro Val Ile Met Glu Leu Glu Arg Gln
        370                 375                 380

Gly Asn Val Leu Val Ile Ser His Gln Ala Val Met Arg Cys Leu Leu
385                 390                 395                 400

Ala Tyr Phe Leu Asp Lys Gly Ala Asp Glu Leu Pro Tyr Leu Arg Cys
            405                 410                 415

Pro Leu His Thr Ile Phe Lys Leu Thr Pro Val Ala Tyr Gly Cys Lys
            420                 425                 430

-continued

```
Val Glu Thr Ile Lys Leu Asn Val Glu Ala Val Asn Thr His Arg Asp
        435             440             445

Lys Pro Thr Asn Asn Phe Pro Lys Ser Gln Thr Pro Val Arg Met Arg
    450             455             460

Arg Asn Ser Phe Thr Pro Leu Ser Ser Ser Asn Thr Ile Arg Arg Pro
465             470             475             480

Arg Asn Tyr Ser Val Gly Ser Arg Pro Leu Gln Pro Leu Ser Pro Leu
            485             490             495

Arg Ala Leu Asp Thr Gln Glu Gly Ala Asp Gln Pro Lys Thr Gln Ala
            500             505             510

Glu Thr Ser Arg Ala Ala His Arg Leu Pro Ser Pro Ala Pro Pro Thr
        515             520             525

Ser Pro Ser
    530
```